(12) United States Patent
Komatsu et al.

(10) Patent No.: US 8,506,965 B2
(45) Date of Patent: Aug. 13, 2013

(54) R-RAS ACTIVITY IN VASCULAR REGULATION

(75) Inventors: Masanobu Komatsu, Orlando, FL (US); David Marshall Mann, San Diego, CA (US); Erkki Ruoslahti, Bueuton, CA (US)

(73) Assignees: Vascular BioSciences, San Diego, CA (US); Sanford Burnham Medical Research Institute, La Jolla, CA (US)

( * ) Notice: Subject to any disclaimer, the term of this patent is extended or adjusted under 35 U.S.C. 154(b) by 842 days.

(21) Appl. No.: 12/093,439

(22) PCT Filed: Nov. 11, 2005

(86) PCT No.: PCT/NL2005/000794
§ 371 (c)(1),
(2), (4) Date: Jun. 3, 2009

(87) PCT Pub. No.: WO2007/055561
PCT Pub. Date: May 18, 2007

(65) Prior Publication Data
US 2009/0304765 A1     Dec. 10, 2009

(51) Int. Cl.
*A61K 39/00*     (2006.01)

(52) U.S. Cl.
USPC ..................................................... 424/198.1

(58) Field of Classification Search
None
See application file for complete search history.

(56) References Cited

U.S. PATENT DOCUMENTS 5,539,085 A * 7/1996 Bischoff et al. ............... 530/350

OTHER PUBLICATIONS

Attwood (Science 290: 471-473, 2000).*
Skolnick et al. (Trends in Biotech. 18: 34-39, 2000).*
Coleman et al. (Nature Reviews: Molecular Cell Biology, 2004, 5:355-366).*
The Merck Manual of Diagnosis and Therapy [online]. Whitehouse Station, NJ, USA. Merck & Co., Inc. 2005 [retrieved on Jul. 30, 2007]. Retrieved from the Internet: <http://www.merck.com/mmpe/print/sec07/ch073/ch073a.html>. Coronary Artery Disease, see Etiology and Pathophysiology.*
Vives, et al. J. Biol. Chem. (1997) 272:16010-16017.
Rajotte, et al. J. Clin. Invest. (Jul. 1998) 102(2):430-437.
Rajotte. et al. Clin. Podiatr. Med. Surg. (Oct. 2003) 20(4):689-708.
Porkka, et al. Proc. Natl. Acad. Sci. USA (May 28, 2002) 99(11):7444-74449.
Christian, et al. J. Cell. Biol. (Nov. 24, 2003) 163(4):871-878.
Rothbard, et al. Natl. Med. (Nov. 2000) 6(11):1253-1257.
Zhang, et al, Circulation (2005) 112:1601-1611.
Ackerman, et al. Proc. Natl. Acad. Sci. USA (Oct. 1, 2002) 99(20):12617-12621.
Kruse, et al. J. Immunol. Methods (Dec. 29, 1997) 210(2):195-203.
O'Connell, et al. Clinical Chem. (1998) 44:1161-1169.
Rothman, A et al., J. Am. Coll, Cardiol. (1996) 27(1):218-224.
Corno. A et al., Eur. J. Cardiothorac Surg. (2003) 23:513-517.
Sinha, et al. Internatl. J. Pharmaceutic (Jun. 18, 2004) 278(1):1-23.
Cole A.L. et al., Arterioscler Thromb Vasc Biol. (2003) 23:1384-1390.
Moiseeva E.P., Cardiovasc. Res. (2001) 52:372-386.

* cited by examiner

*Primary Examiner* — Sharon Wen
(74) *Attorney, Agent, or Firm* — Lewis Kohn & Fitzwilliam LLP; David M. Kohn; Kari Moyer-Henry

(57) ABSTRACT

The invention provides means and methods for vascular regulation through enhancement or inhibition of R-Ras activity. The invention specifically provides means and methods for promoting a quiescent state of a vascular cell by providing additional R-Ras activity to the cell. The invention further provides means and methods for diagnosing a condition of vasculature of an individual.

6 Claims, 17 Drawing Sheets

R-Ras_wt 1 mssgaasgtg  rgrprgggpg  pgdpppseth  klvvvggggv  gksaltiqfi
qsyfvsdydp
     61 tiedsytkic  svdgiparld  ildtagqeef  gamreqymra  ghgfllvfai
ndrqsfnevg
    121 klftqilrvk  drddfpvvlv  gnkadlesqr  qvprseasaf  gashhvayfe
asaklrlnvd
    181 eafeqlvrav  rkyqeqelpp  sppsaprkkg  ggcpcvll R-Ras 38V The sequence of R-Ras_wt, wherein glycine at position 38 is
substituted with valine.

R-Ras 87L

The sequence of R-Ras_wt, wherein glutamine at position 87 is
substituted with leucine.

R-RAS ACTIVITY IN VASCULAR REGULATION

GRANT INFORMATION

Certain work described herein was supported, in part, by U.S. Federal Grant Nos. PO1 CA82713, RO1 CA79984, T32 CA09579, and P30 CA30199, awarded by the National Institutes of Health. The United States Government may have certain rights in the invention. All references noted herein are hereby incorporated by reference.

PRIORITY APPLICATION

This application is a U.S. National Stage under 35 U.S.C. 371 of international application no. PCT/NL05/11794.

BACKGROUND

The invention relates to the field of vascular regulation and to the role of R-Ras in vascular regulation. The invention in particular relates to means and methods for promoting a quiescent state for a vascular cell and to means and methods for diagnosing a condition of vasculature of an individual. More in particular the invention relates to RAS proteins or functional equivalents thereof, as well as their genes, particularly in gene therapy settings for providing RAS-activity to vascular cells.

The Ras family of small GTPases comprises intracellular signaling molecules that function as binary switches regulated by GTP. The oncogenic Ras proteins, H-Ras, and K-Ras in particular, are central players in cellular signaling networks; they are activated by most growth factors as well as by integrins. R-Ras is a member of the Ras protein family that antagonizes H-Ras signaling[1,2]. Due to its sequence homology with the prototypic Ras proteins, R-Ras has been often described as a transforming oncogene[3]. The transforming activity of R-Ras in vitro is, however, quite low compared with that of H-Ras and K-Ras[4], and there is no evidence that activating mutations would occur in spontaneous malignancies. Moreover, R-Ras differs from the other members of the Ras family in that it contains a proline-rich SH3 domain binding site, within which it can be phosphorylated by Eph receptors and Src; both SH3 domain binding and phosphorylation regulate R-Ras activity[5-7].

The present invention makes use of the finding that R-Ras has different properties than the more conventional Ras proteins/genes. R-Ras and H-Ras for instance exert opposite effects on cell-extracellular matrix adhesion; R-Ras enhances integrin-mediated cell adhesion by elevating the affinity and avidity of integrins[8], whereas H-Ras inhibits integrin activities[9]. There is also a striking contrast in R-Ras and H-Ras activities in cell differentiation. R-Ras promotes the differentiation of myoblasts and the fusion of these cells to myotubes, a process that requires cell cycle arrest and entry to G0 state[10], whereas H-Ras inhibits these processes[11]. The in vivo function of R-Ras, however, has formerly remained unclear. The invention surprisingly discloses that R-Ras is a vascular regulator. In particular, R-Ras is a regulator of vascular differentiation that primarily affects the remodeling of blood vessels.

The invention in one embodiment provides a method for promoting a quiescent state for a vascular cell, comprising providing said cell with additional R-Ras activity. A quiescent state for a vascular cell as used in the invention is a state wherein the cell cycle of a vascular cell is arrested and/or wherein a cell is in the G0 state. Promoting means that the process of cell cycle arrest is enhanced and/or that the entrance of a cell into the G0 state is stimulated. Further, promoting means that a cell that is in a quiescent state is stimulated to maintain the quiescent state. A quiescent state of a vascular cell means that cell proliferation and migration is inhibited and further that the cell is in a state that facilitates differentiation. There are many instances wherein it would be very favourable to promote a quiescent cell state in a vascular cell. For instance, in tumors, in hyperplastic arterial lesions, in pulmonary hypertension, pulmonary vascular diseases, organ transplant rejection, peripheral artery disease, coronary artery disease, collagen vascular diseases such as lupus and scleroderma, vasculitis and autoimmune diseases. An additional R-Ras activity is any amount of activity that raises the activity of a cell above the initial level. Thus, in a cell wherein R-Ras activity was for example absent, or alternatively, was present but at a lower level. A vascular cell as used in the invention is preferably an endothelial cell or a smooth muscle cell. R-Ras activity can be added by any means or method that enhances the presence or activity of R-Ras or a functional equivalent thereof in a vascular cell. This can be achieved directly by providing R-Ras protein or a functional equivalent thereof or indirectly by providing an expressible nucleic acid which can express R-Ras activity and/or by activating a pathway in a vascular cell that leads to expression of R-Ras activity (in particular of a R-Ras protein), or activation of pre-existing R-Ras.

In one embodiment of the invention additional R-Ras activity is provided through activation of inactive R-Ras in a cell. The activity of Ras proteins is in one aspect controlled by the balance of GTP and GDP bound to the protein, wherein the GTP-bound form is active and the GDP-bound form is inactive. Activation is for instance established by stimulating the binding of GTP to the R-Ras protein. In one embodiment of the invention additional R-Ras activity is provided by converting GDP-bound R-Ras protein into GTP-bound R-Ras protein, by phosphorylating said GDP. As the R-Ras protein itself is a GTPase, its activity is further regulated by accessory proteins that influence the activity of the GTPase functionality. In a further embodiment of the invention additional R-Ras activity is thus provided by inhibiting or enhancing presence and/or activity of accessory proteins. In an alternative embodiment of the invention post-translational modification by lipid attachment is enhanced to provide additional R-Ras activity or post-translational modification by lipid attachment is inhibited to reduce R-Ras activity. Post-translational modification of R-Ras protein in order to make the protein functional is, for instance, farnesyl or geranyl attachment. R-Ras has a further regulation mechanism that is typical for R-Ras compared to the other Ras proteins. R-Ras differs from the other members of the Ras family in that it contains a proline-rich SH3 domain binding site, within which it can be phosphorylated by Eph receptors and Src. Eph receptors and Src are both protein tyrosine kinases (PTKs). Protein tyrosine kinases (PTKs) are enzymes which catalyze the phosphorylation of tyrosine residues. PTKs are involved in cellular signaling pathways and regulate key cell functions such as proliferation, differentiation, anti-apoptotic signaling and neurite outgrowth. There are two main classes of PTKs: receptor PTKs and cellular, or non-receptor, PTKs. Cellular PTKs, such as Src, are located in the cytoplasm, nucleus or anchored to the inner leaflet of the plasma membrane. Receptor PTKs possess an extracellular ligand binding domain, a transmembrane domain and an intracellular catalytic domain. Eph receptors form the largest subfamily of receptor tyrosine kinases (RTKs). Both SH3 domain binding and phosphorylation regulate R-Ras activity[5-7]. Thus in one embodiment of the invention R-Ras activity is added by enhancing binding of SH3 domains to a proline-rich site of R-Ras. In a preferred embodiment, regulation of R-Ras activity is provided by enhancing or inhibiting presence of R-Ras protein, as the amount of protein is a stronger regulator of R-Ras activity in a cell than internal activating or inhibiting mechanisms of R-Ras protein.

The invention in a preferred embodiment provides a method according to the invention, wherein said activity is provided by an R-RAS protein and/or a functional equivalent thereof. A functional equivalent is any equivalent having the same function in kind, not necessarily in amount. A sequence of wild type R-Ras protein is given in FIG. 14. For further characterization and expression of the Human R-Ras gene product, see for example ref. 51. R-Ras proteins have little or no species specificity. Wild type and mutant R-Ras proteins found in an animal are thus applicable in many other species. A functional equivalent is for example a synthesized artificial R-Ras protein, a recombinant and/or a mutant R-Ras protein. Examples of such mutants are R-Ras 38V and R-Ras 87L. Such mutants are optionally combined to derive a potent R-Ras protein. In another embodiment of the invention additional R-Ras activity is provided by introduction of a nucleic acid encoding an R-Ras protein or a functional equivalent thereof. An alternative means to provide additional R-Ras activity is enhancing R-Ras gene transcription and/or translation e.g. by stimulating a promoter sequence of R-Ras.

In an alternative embodiment of the invention R-Ras activity in a vascular cell is reduced. Reduction of R-Ras activity in a vascular cell is for example established by down-regulating R-Ras expression in the cell or by degrading R-Ras protein and/or R-Ras mRNA in a cell, and by promoting hydrolysis of GTP bound to R-Ras to GDP or by preventing the modification of R-Ras by lipid attachment. Down-regulating is for example established by an antisense-technique. Non-limiting examples of some of the newer antisense approaches are interference RNA (RNAi), microRNA and splice interference techniques such as exon-skipping. Reducing R-Ras activity in a cell stimulates proliferation and migration and diminishes differentiation of the cell. Angiogenesis is thus stimulated by down-regulation of R-Ras activity. Indications for down-regulating R-Ras activity in a cell are for example rehabilitation of an infarct, a stroke or of organ or limb damage. Balancing down- and up-regulation of R-Ras activity is a method for structuring modeling of vasculature. The invention in one embodiment provides a method for structuring modeling of vasculature, comprising providing said cell with additional R-Ras activity or reducing R-Ras activity in said cell. Modeling herein proceeds through stimulation/inhibition of cell growth, differentiation, proliferation and migration.

In one embodiment of the invention, R-Ras activity is added or reduced by intervening in an R-Ras pathway. The results of examples of the invention demonstrate that the effect of R-Ras on vascular cell activities is mediated, at least in part, by inhibitory phosphorylation of Raf-1. Other pathways do, however, also play a role. In a preferred embodiment of the invention R-Ras activity is added by enhancing inhibitory phosphorylation of Raf-1, or reduced by diminishing inhibitory phosphorylation of Raf-1. Raf-1 is at least part of a PI3-kinase-Akt signaling pathway. In one embodiment of the invention R-Ras activity is enhanced by activating at least a subset of Akt molecules or reduced by inhibiting at least a subset of Akt molecules.

An R-Ras protein is produced in any prokaryotic or eukaryotic cell. Delivering an R-Ras protein to a cell is done by any means that transports the protein/peptide into a cell. For example by electrotransfection, electroporation or through delivery by a cell penetrating peptide. Alternatively, R-Ras protein is delivered comprised in a nanoparticle. In a preferred embodiment the invention provides a method according to the invention, wherein said R-Ras protein or said functional equivalent thereof is provided with a cell penetrating peptide. There are many types of cell penetrating peptides available in the art. For references, see for example ref. 52-55. Any type of cell penetrating peptide that delivers R-Ras protein or a functional equivalent thereof can be used according to the invention. A cell penetrating peptide is for example a protein derived peptide, such as penetratin, a Tat-derived peptide, a signal-sequence-based peptide (I or II), or a synthetic and/or chimeric cell-penetrating peptide such as transportan or an amphiphilic model peptide. Specific preferred examples of such cell penetrating peptides are Tat, a cell penetrating peptide (refs. 96-98); F3 (ref. 95), an internalizing tumor specific homing peptide; and Arginine Heptamer (refs. 99-104), which is a dermis penetrating peptide.

In a further preferred embodiment the invention provides a method according to the invention, wherein said R-Ras protein or said functional equivalent is provided with a homing peptide. A homing peptide is any peptide that targets a cell of a selected tissue. In the art many homing peptides are available. In a preferred embodiment the homing peptides are lung homing peptides, heart homing peptides or tumor homing peptides. Heart homing peptides are for example a CRPPR (SEQ ID NO:1) peptide that at least binds to a Cysteine-rich protein 2 receptor, and a CPKTRRVPC (SEQ ID NO:2) peptide that at least binds to a bc10 receptor. For further references for heart homing peptides see for instance ref 56, specifically the table on page 1605. Lung homing peptides are for example Metadherin or GFE-1 (CGFECVRQCPERC (SEQ ID NO:3)). For further references for lung homing peptides see for instance refs 57, 58 and 105-110. Preferred tumor-homing peptides are for example F3, a 34-amino acid basic peptide (see further refs. 59, 60); CGKRK (SEQ ID NO:4) (see under more refs. 61 and 62); and LyP-1, sequence CGNKRTRGC (SEQ ID NO:5) (see for instance refs. 63 and 64). Relevant tumor homing peptides are further for instance described in refs 59-64. Preferably a homing peptide homes to lung, heart, especially a coronary artery, or any vasculature. The cell penetrating peptides and/or homing peptides can be attached to the protein providing R-Ras activity by any conventional means. An easy way of preparing the complex is through producing a vector encoding a fusion of R-Ras protein with a cell penetrating peptide and/or a homing peptide and expressing said vector in a suitable host as disclosed in the examples.

In one embodiment the invention provides R-Ras or a functional equivalent thereof for use as a medicine. The medicine is used for any occasion wherein it is desired to promote a quiescent state for a vascular cell. In a preferred embodiment R-Ras or a functional equivalent thereof is used in the preparation of a medicament to promote a quiescent state for a vascular cell. A medicament is any pharmaceutical composition comprising R-Ras or a functional equivalent thereof. Such a pharmaceutical composition optionally further comprises a pharmaceutically acceptable carrier and any additive. A medicine is for example produced as a pill, a capsule, a tablet, a medicinal gum, a solution, a dry powder form, an inhaler, transdermal patch, microsphere, nanocrystal, or as a coating for a device that is introduced in a body within contact of vasculature.

In one embodiment the invention provides a protein complex comprising R-Ras or a proteinaceous functional equivalent thereof and a cell penetrating peptide and/or a homing peptide. Such a protein complex is for example a fusion protein or a complex which is held together by disulfide bonds. In a preferred aspect of the invention a protein complex according to the invention is a fusion protein. There are diverse chemical coupling methods available in the art for the production of a fusion protein, a fusion protein of the invention is produced by any of these methods. An example of such a fusion protein is a fusion protein of R-Ras or R-Ras mutant 38V or 87L and a Tat-derived peptide. In one embodiment of the invention, a homing peptide is a part of a fusion protein. A functional equivalent as used in the invention is at least functionally the same in kind as R-Ras, though not necessarily the same in amount. The invention further provides a nucleic acid molecule comprising a nucleic acid sequence coding for a fusion protein according to the invention. A nucleic acid is for example a DNA, RNA or PNA. In an alternative embodiment of the invention, R-Ras is comprised in a nanoparticle. For this embodiment, R-Ras does not have to be modified, but can be if desired. A homing peptide is optionally attached to the particle core.

In one aspect the invention provides a gene delivery vehicle encoding R-Ras or a functional equivalent thereof. In a further embodiment the invention provides a gene delivery vehicle encoding a fusion protein according to the invention, or comprising a nucleic acid molecule according to the invention. A gene delivery vehicle is any vehicle that delivers a gene encoding an R-Ras or functional equivalent thereof to a cell. Preferably said cell is a vascular cell, more preferably an endothelial or a smooth muscle cell. A gene delivery vehicle is in a preferred embodiment a vector encoding R-Ras or a functional equivalent thereof. A vector is preferably an expression vector wherein R-Ras or a functional equivalent thereof is operatively linked to an enhancer sequence and/or a promoter sequence. Transduction of a vector according to the invention is for example mediated through a virus. Non-limiting examples of such viruses are an adenovirus, an adeno associated virus, an alphavirus such as sindbis or SFV a lentivirus and/or a retrovirus. Non-viral delivery vehicles include polymers and/or liposomes or other nanoparticles (based on e.g. biodegradable polymers).

In a preferred embodiment the invention provides an article of manufacture to be introduced into an environment comprising vascular cells, coated with a composition comprising R-Ras or a functional equivalent thereof, or a composition comprising a protein complex according to the invention, or a composition comprising a gene delivery vehicle according to the invention. Coated as used in the invention means that the additional R-Ras activity is available to the environment comprising vascular cells. Coated means preferably, but not necessarily, that the layer of the article of manufacture exposed to the environment is provided with additional R-Ras activity. Such an article of manufacture is introduced in any environment wherein additional R-Ras activity is beneficial. Additional R-Ras activity is for example beneficial in an environment where cell migration and proliferation, in particular of vascular cells, is undesirable. Providing additional R-Ras activity is for example beneficial in order to prevent a hyper-reactive response of an organism to an external device that is inserted in said organism. Adding R-Ras activity at least partially inhibits vascular cell proliferation and migration as a response to an external stimulus. Another example of a circumstance wherein adding R-Ras activity is beneficial, is in the case of tumor growth. R-Ras activity then prevents angiogenesis in and adjacent to the tumor, thereby inhibiting the blood supply to the tumor tissue. In addition, adding R-Ras activity increases cell adhesion. In one embodiment the invention provides use of R-Ras or a functional equivalent thereof, for stimulating adhesion of vascular endothelial cells to a vessel wall. Increasing cell adhesion can further, for instance, convert a leukemia into a lymphoma or inhibit metastasis. Increasing cell adhesion through R-Ras is at least partially mediated by integrins. In a preferred embodiment the invention provides an article of manufacture to be introduced into an environment comprising vascular cells, coated with a composition comprising R-Ras or a functional equivalent thereof, or a composition comprising a protein complex according to the invention, or a composition comprising a gene delivery vehicle according to the invention, further comprising a Tat peptide and/or a homing peptide. In a further preferred embodiment said article of manufacture is a stent.

An article of manufacture of the invention is any article of manufacture that is in any instance introduced into an environment comprising vascular cells. Such an article is for example a device that forms a portal in a mammal. Such a portal is for instance a portal to a bowel, a stomach, a bladder, an esophagus or a trachea. Alternatively, an article of the invention is a device that is placed internally in an environment that comprises vascular cells. An internally placed article is for example an artificial heart-valve. In a preferred embodiment of the invention an article of manufacture according to the invention is a stent. A stent as used in the invention is a device that is open in that there is passage possible for bodily fluids and that is inserted in an organism, preferably a mammal. A stent is preferably a small tube that is inserted for more than 6 hours, preferably for longer, in a preferred embodiment permanently, in an organism. In a preferred embodiment the stent is introduced in an artery. The stent at least assists in holding open an artery so that blood can flow through it. In a preferred aspect a stent is an intraluminal coronary artery stent. Such a stent is typically used in angioplasty, which is a procedure to reduce or eliminate blockages in coronary arteries.

In one embodiment the invention provides a composition for promoting a quiescent state for a vascular cell, comprising R-Ras or a functional equivalent thereof, a protein complex according to the invention, or a gene delivery vehicle according to the invention.

Such compositions can be pharmaceutical compositions, cosmetic compositions or compositions for use on cells in vitro. These compositions can therefore comprise the conventional usual excipients, buffers and other constituents for such compositions. The invention in another embodiment provides a composition according to the invention, further comprising a $2^{nd}/3^{rd}$ active agent. In a further embodiment the invention provides such a composition whereto a $4^{th}$, $5^{th}$, or any further active agent is added. An active agent is any active agent that is beneficially combined with R-Ras activity in a composition. Such a composition is for instance a pharmaceutical that is intended for treatment and/or prevention of vascular narrowing. Further active agents in the composition are, for that indication, for instance heparin or another anticoagulant or acetylsalicylic acid. Vascular narrowing is for example a problem in a patient with post-angioplasty restenosis or artherosclerosis. In a further preferred embodiment the invention provides a composition according to the invention, further comprising sildenafil citrate, sirolimus, and/or Gleevec.

Preferred active agents in a composition of the invention are:
  Diuretics, sometimes called "water pills". These agents flush excess water and sodium from the body by increasing urination. This reduces the amount of fluid in the blood and flushes sodium from the blood vessels so that they can open wider, increasing blood flow and thus reducing the blood's pressure against the vessels. Diuretics are optionally used in combination with other high blood pressure drugs. Types of diuretics include thiazides, such as Diuril (chlorothiazide) and Esidrex (hydrochlorothiazide); potassium-sparing diuretics, such as Aldactone (spironolactone); and loop diuretics, such as Lasix (furosemide).

Beta blockers. These agents slow the heartbeat by blocking the effect of nerve impulses to the heart and blood vessels, thereby lessening the burden on the heart. Beta blockers include Inderal (propranolol), Lopressor (metoprolol), and Tenormin (atenolol).

ACE (angiotensin-converting enzyme) inhibitors. These agents inhibit formation of the hormone angiotensin II, which causes blood vessels to narrow, thus increasing blood pressure. ACE inhibitors include Altace (ramipril), Capoten (captopril), and Zestril (lisinopril).

Calcium channel blockers. These agents prevent calcium from entering the muscle cells of the heart and blood vessels, thus relaxing blood vessels and decreasing blood pressure. Some calcium channel blockers are Procardia (nifedipine), Isoptin (verapamil) and Cardizem (diltiazem).

Alpha-beta blockers. These agents combine the actions of alpha blockers, which relax blood vessels, and beta blockers, which slow the heartbeat. The dual effect reduces the amount—and thus pressure—of blood through blood vessels. Alpha-beta blockers include Normodyne and Trandate (both labetalol).

Diuretics, beta blockers, ACE inhibitors, calcium channel blockers and alpha-beta blockers and functional analogues and derivatives of these agents are preferably used in the case of hypertension, more preferably in the case of systemic hypertension. The functional analogues or derivatives as used in the invention have a function that is the same in kind, not necessarily the same in amount.

Active agents that are specifically preferred in a composition of the invention for use in case of pulmonary hypertension are: epoprostenol, treprostinil, bosentan, sildenafil, iloprost, sitaxsentan, and Ambrisentan, or functional analogues or derivatives thereof. Preferred active agents in a composition of the invention for use in case of need of an antiproliferative, for instance in cancer, are: Methotrexate, Fluorouracil, cisplatin, doxorubicin, 5-fluotacil; VEGF inhibitors such as bevacizumab (Avastin); Protein kinase inhibitors such as imatinib (Gleevec); and epidermal growth factor receptor tyrosine kinase inhibitors such as erlotinib (Tarceva) and gefitinib (Iressa), or functional analogues or derivatives of these agents. Preferred agents in a composition of the invention for use in stent coatings are: Sirolimus, Tacrolimus, Paclitaxel, Everolimus, or functional analogues or derivatives thereof.

In one embodiment a composition according to the invention is a pharmaceutical composition optionally further comprising additives, such as a pharmaceutically acceptable carrier or a colorant.

In a preferred embodiment the invention provides a composition, which is a controlled release composition. A controlled release composition as used in the invention is any composition that does not release all activity at one point in time. A controlled release composition of the invention preferably constantly releases approximately even amounts of active agent for a longer period of time. A longer period of time are preferably hours, more preferably days, and most preferred weeks, months or years. A controlled release composition of the invention is typically a biodegradable composition. A controlled release composition is for example produced in the form of a biodegradable microsphere (see for example ref. 65). A controlled release composition of the invention is for example used in a coated article of manufacture of the invention, such as a stent. Adding a controlled release composition of the invention to for instance a heart atrioventricular valve will reduce vessel proliferation on implantation of the valve in for example a mammal. Thereby adding such a composition at least partially helps to prevent the forming of an obstructive mass in a blood stream.

In one embodiment the invention provides a method for diagnosing a condition of vasculature of an individual, comprising obtaining a sample from said individual and measuring an expression level of R-Ras expression in said sample. A condition of vasculature as used herein is a status of health or development of vasculature of an individual, such as a pathological or a physiological status. Furthermore the status refers characteristics of the vasculature such as the differentiation state of a cell or of multiple cells. A sample as used in the invention is for example a sample of a bodily fluid, such as blood or lymph. A sample is alternatively obtained from a bronchoalveolar lavage (BAL), Transbronchial biopsy (TBB), or Endomyocardial heart biopsy. In a preferred embodiment a sample is a vascular cellular sample. A vascular cellular sample of the invention is any sample comprising cells that were located adjacent to or part of a vascular tissue. A vascular cellular sample is preferably derived from one of the larger vessels in an animal. Preferably said larger vessel is an artery. In a preferred embodiment a vascular cellular sample is obtained from a mammal, preferably a human being. A vascular sample as used in the invention is obtained with any method for taking a vascular cellular sample. Such a method is for example a surgical method or a minimal invasive method such as a cheek mucosal tissue sampling technique. In a preferred embodiment of the invention a sample in a method for diagnosing a condition of vasculature of an individual is obtained with a percutaneous endoarterial biopsy, a percutaneous atherectomy, or another surgical method.

An expression level of R-Ras can be measured in alternative ways. An expression level of R-Ras can be measured from any product of an R-Ras mRNA. For example the level of R-Ras protein, or the level of a derivative of R-Ras protein is measured. An expression level of R-Ras is for example performed through an immunodetection technique, such as immunohistochemistry, immunofluorescence or immunoblotting. Alternatively expression levels are determined with a PCR technique, for instance quantitative real time PCR. In the art many other techniques for determining an expression level are available, such as multiple microarray techniques. In a preferred embodiment a method according to the invention is provided, wherein measuring is performed through PCR, a microarray technique, immunohistochemistry, immunofluorescence or immunoblotting.

In one embodiment the invention provides a method for diagnosing a condition of vasculature of an individual, wherein said condition of vasculature of said individual is associated with a disorder in said individual and wherein said disorder is a vascular proliferative disease. Diagnosis is either directed to a local, a regional or a systemic condition of vasculature of an individual. A vascular proliferative disorder is any disease wherein vasculature of an individual proliferates. Proliferation typically refers to cell multiplication, but generally, as in most vascular proliferative disorders, it also involves growth of at least some individual cells. Non-limiting examples of vascular proliferative disorders are: idiopathic pulmonary hypertension, chronic hypoxic pulmonary hypertension, systemic hypertension, atherosclerosis, post-angioplasty restenosis, vasculopathy, diabetic vasculopathy, vascular injury, vasculitis, arteritis, capillaritis or carcinoma.

In a preferred embodiment, the invention provides a method for diagnosing a condition of vasculature of an individual, wherein said vascular proliferative disease is selected from the following: pulmonary hypertension, carcinoma or vascular injury.

The invention provides a kit for diagnosing a condition of vasculature of an individual, at least comprising a means for measuring an expression level of R-Ras in a sample and an apparatus for obtaining a sample. An apparatus for obtaining a sample is any device that can be used to derive a sample as defined by the invention. A non-limiting example of such an apparatus is a syringe or syringe-like device or a catheter or biopsy device. In a preferred embodiment of the invention, an apparatus for obtaining a sample is an atherectomy catheter or an endoarterial biopsy device.

The invention further provides a kit according to the invention, wherein the means for measuring an expression level comprises a binding body and a detection reagent. Many different specific binding bodies are available. Of old, antibodies are used. However, currently many different parts, derivatives and/or analogues of antibodies are in use. Non-limiting examples of such parts, derivatives and/or analogues are, single chain Fv-fragments, monobodies, VHH, Fab-fragments and the like. A common denominator of such specific binding bodies is the presence of an affinity region (a binding peptide) that is present on a structural body that provides the correct structure for presenting the binding peptide. Binding peptides are typically derived from or similar to CDR sequences (typically CDR3 sequences) of antibodies, whereas the structure providing body is typically derived from or similar to framework regions of antibodies. A detection reagent is any reagent that provides detection of binding or non-binding of an antibody. A detection reagent for example comprises a reporter group or is a fluorescent marker.

Microvessel infiltration into matrigel plugs was determined by MECA32 staining and quantified (six animals/group). Control, mock infection with empty vector. g, VEGF-induced microvessel sprouting from R-Ras-null aorta rings was suppressed ex vivo by infection of the lentivirus carrying activated R-Ras genes. Control, mock infection control. Data is presented as microvessel count relative to the control at day 4.

Figure 6:
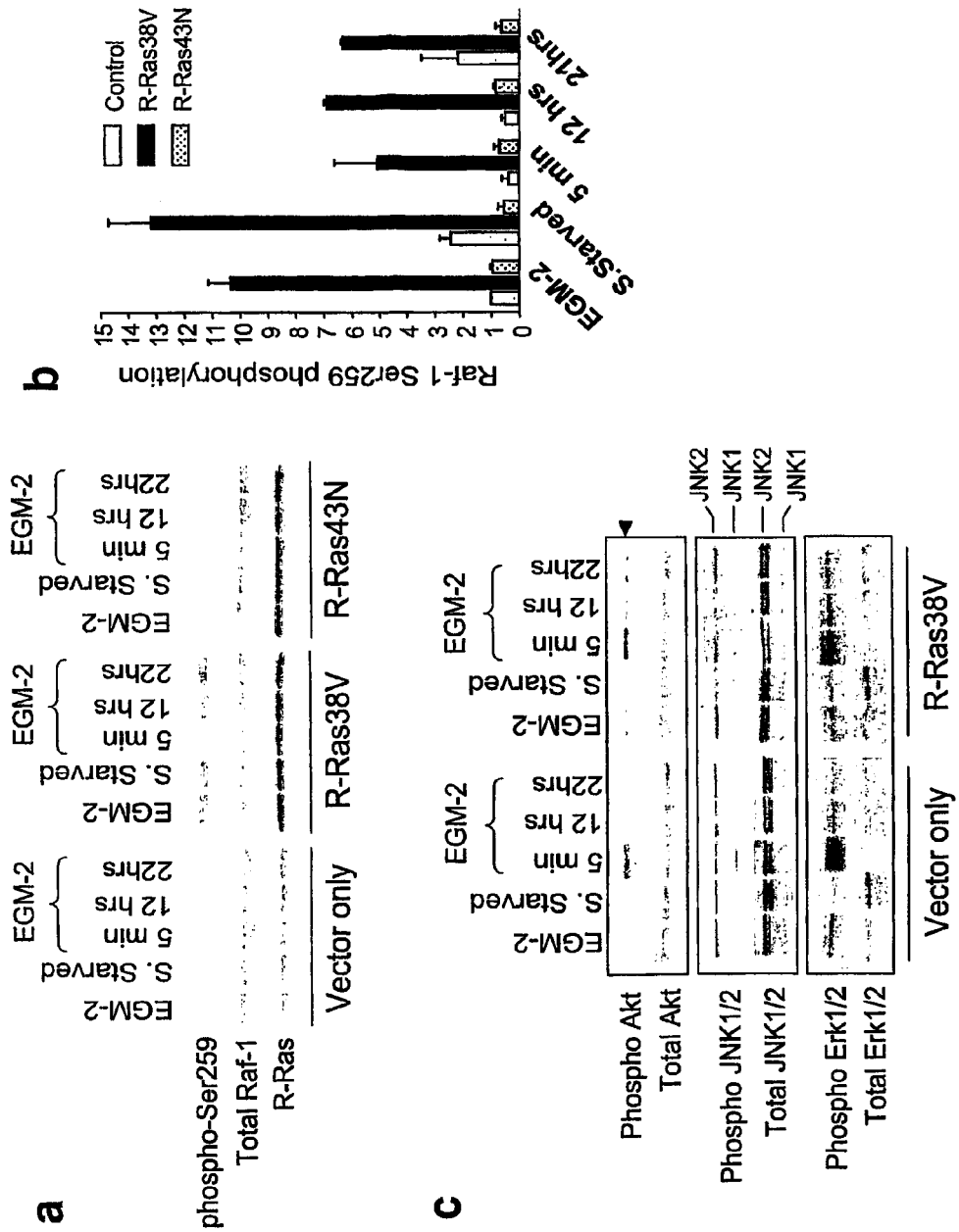

FIG. 6. R-Ras signaling induces the inhibitory phosphorylation of Raf-1. a. The transduced HUVEC were cultured in the mitogen-rich endothelial growth media EGM-2. They continued to be cultured in EGM-2, starved for mitogens/serum for 14 hours, or starved then stimulated with EGM-2 for the indicated time before harvested for immunoblot analyses. The state of inhibitory phosphorylation of Raf-1 was determined by using polyclonal antibody against phosphorylated Ser259 of Raf-1. b. The level of Ser259 phosphorylation was quantified by densitometry, normalized for the total Raf-1 expression, and presented relative to the level in the vector-only control cells cultured in EGM-2 media. Three independent experiments were performed. Mean and standard error of mean (error bar) are shown. c. Activation of Akt, JNK1/2, and Erk1/2 was assessed by detecting phosphorylation at Ser473 (arrowhead), Thr183/Tyr185 (JNK1/2), and Thr202/Tyr204 (Erk1/2) using phospho-specific antibodies.

Figure 7:
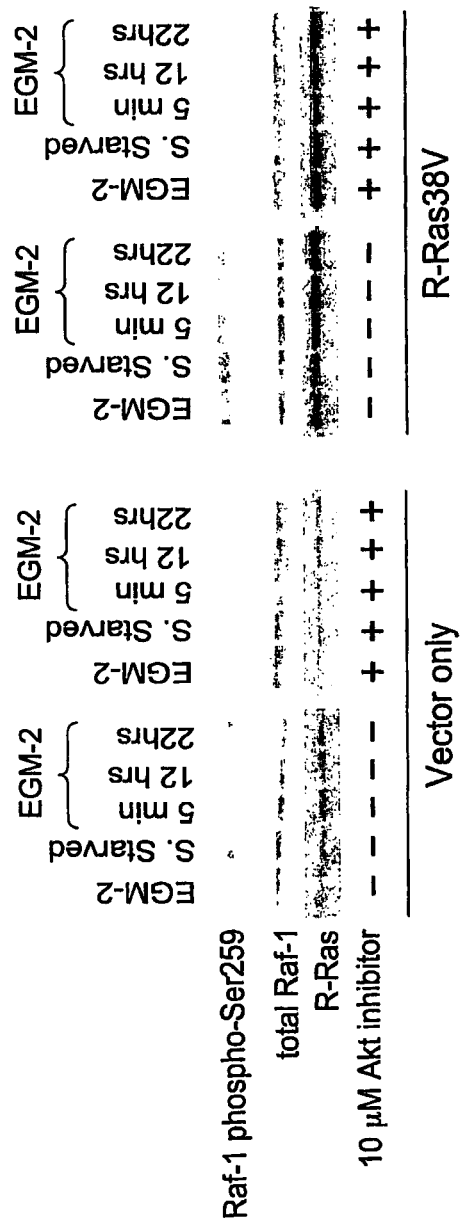

FIG. 7. Akt mediates R-Ras-induced Raf-1 phosphorylation. The state of Raf-1 Ser259 phosphorylation was determined with and without Akt inhibition. Transduced HUVEC were treated with 10 .mu.M Akt inhibitor (Calbiochem) in EGM-2 media for several hours or treated for 1.5 hours in starvation media prior to the stimulation, followed by transfer to EGM-2 media containing 10 .mu.M Akt inhibitor. Only basal levels of Ser259 phosphorylation were detected in the inhibitor-treated cells.

Figure 8:
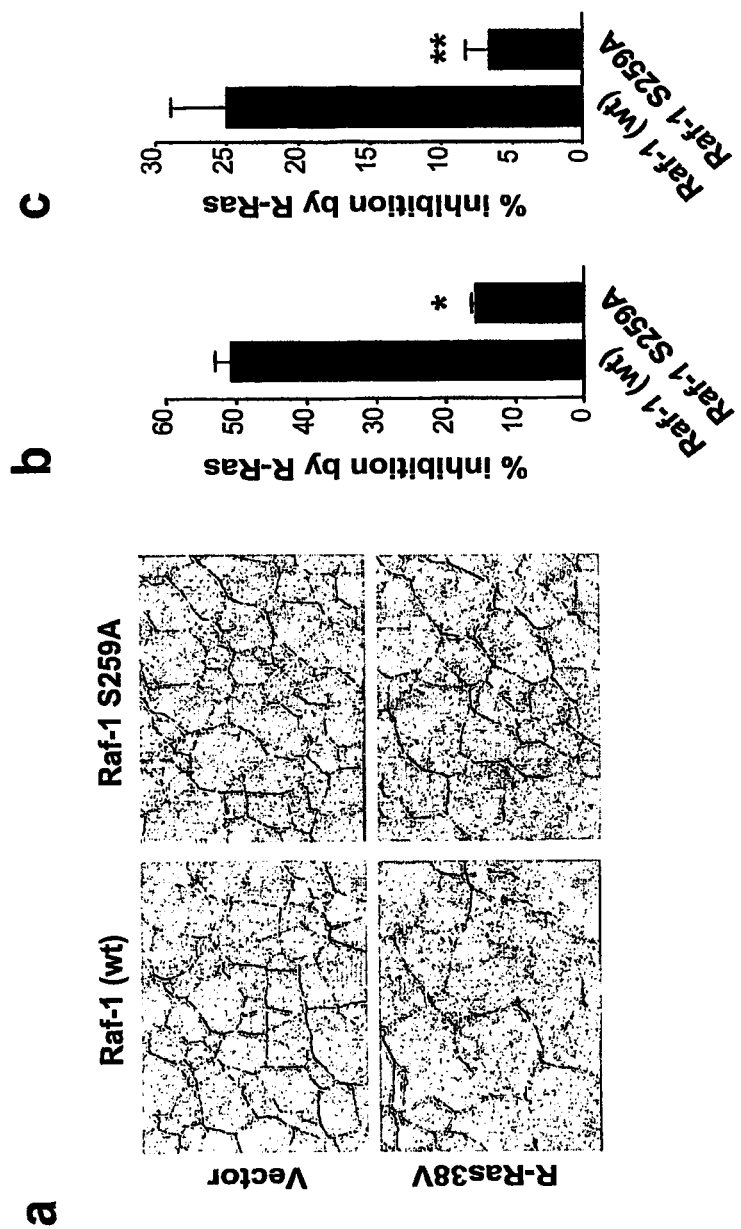

FIG. 8. Raf-1 S259A mutation blocks the inhibitory effect of R-Ras on HUVEC tube formation and proliferation. a. micrographs of endothelial tubes formed by the HUVEC transduced first with wild-type Raf-1 (wt) or Raf-1 S259A mutant and subsequently with R-Ras38V or empty vector (Vector). b. The efficiency of tube formation was quantified and % inhibition by R-Ras was determined. *P<0.005. c. the same cell populations were seeded onto 48-well plates to assess inhibition of proliferation by R-Ras during 2-day culture in EGM-2 media. Percent inhibition by R-Ras was compared in cells expressing wild-type Raf-1 (wt) or Raf-1 S259A. **P=0.01.

Figure 9:
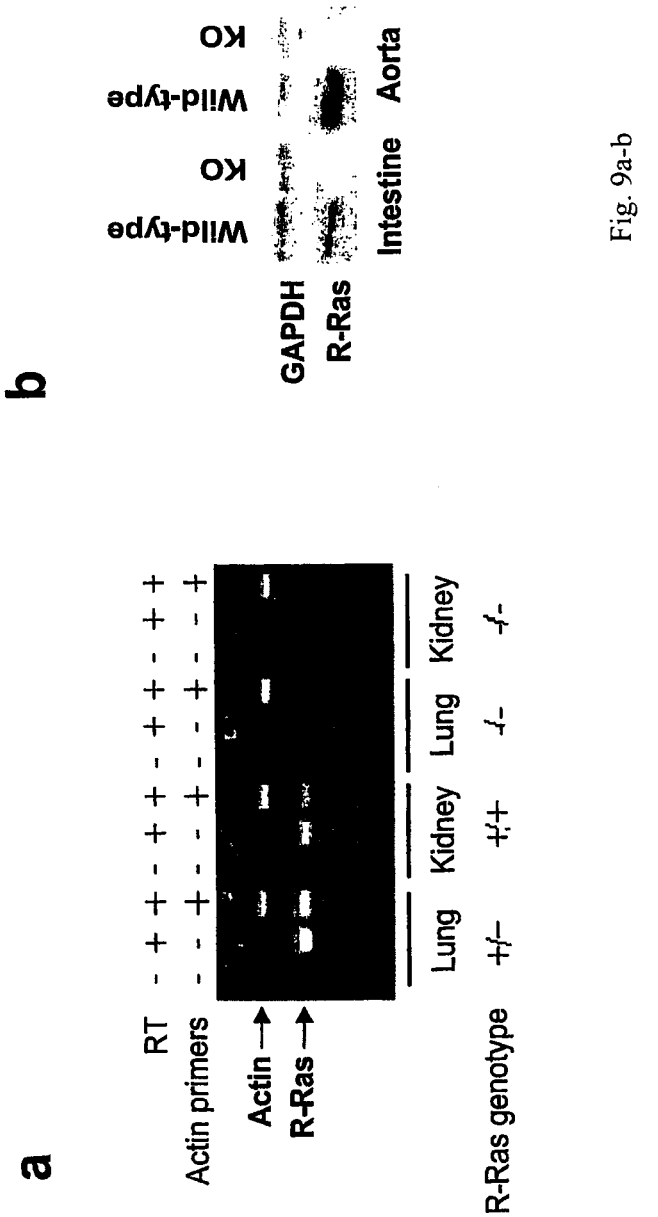

FIG. 9. Absence of intact R-Ras mRNA and protein expression in R-Ras-null mice. a, R-Ras mRNA was analyzed by RT-PCR of from lung and kidney extracts. R-Ras specific primer set was: AGGCAGAGTTTCAATGAG-GTGGGCAAGCTC (forward (SEQ ID NO:6)), CTCATC-GACATTCAGACGCAGTTTG (reverse (SEQ ID NO:7)). Actin primer set was used in parallel as an internal control. No-RT reaction sample (RT-) was used as negative control. b, R-Ras expression was determined by anti-R-Ras immunoblotting of SDS extracts of tissues. GAPDH was used as loading control.

Figure 10:
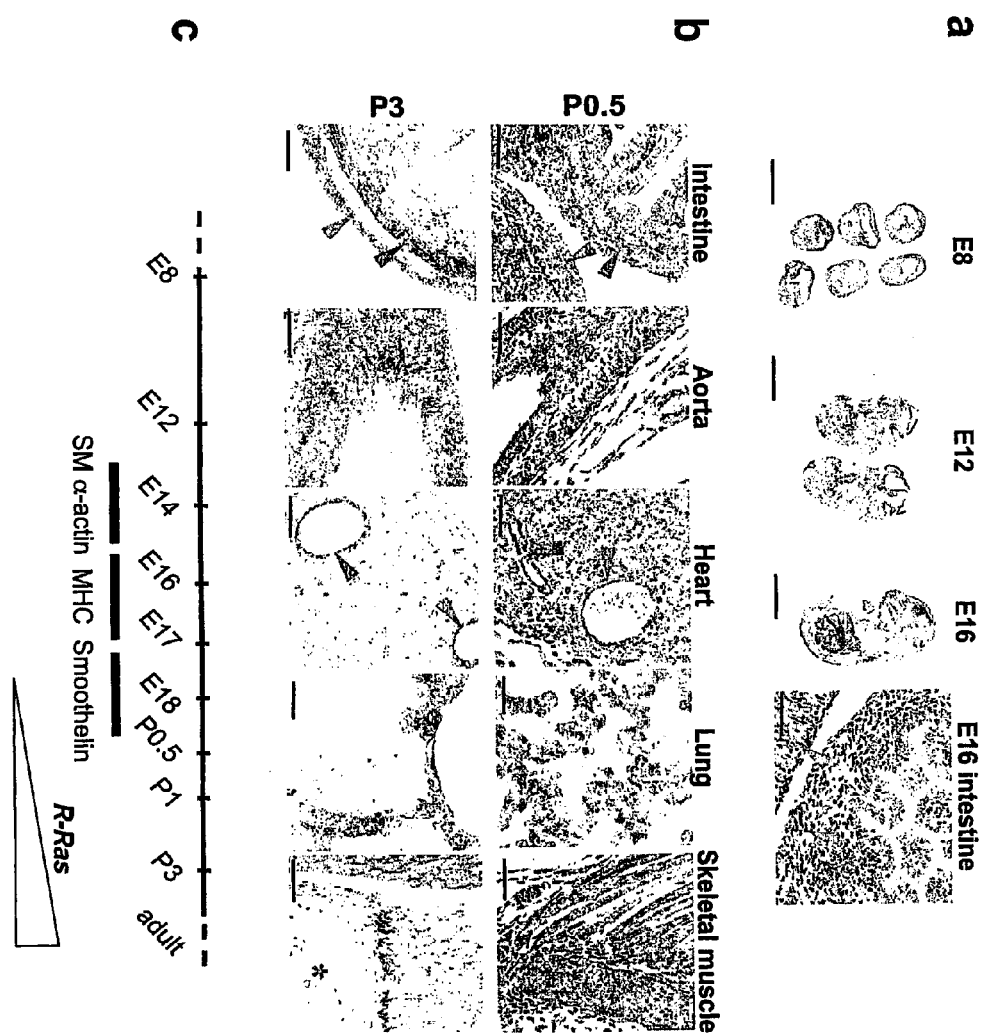

FIG. 10. Spatio-temporal pattern of R-Ras expression during mouse development. a. Day 8-16 mouse embryo (E8-E16) sections were stained with anti-R-Ras antibodies. Scale bar, 0.5 mm for whole mount embryos, 50 µm for section of E16 intestine. Arrowheads indicate layers of SMC. b. Neonatal expression in P0.5 (postnatal day 0.5) and P3 intestine, aorta, heart, lung, and skeletal muscle. Arrowheads, layers of SMC; *, bone; scale bar, 50 µm except for lung (20 µm). c. Summary of R-Ras expression in smooth muscle relative to other SMC markers during development. SM α-actin, smooth muscle α-actin; MHC, smooth muscle myosin heavy chain.

Figure 11:
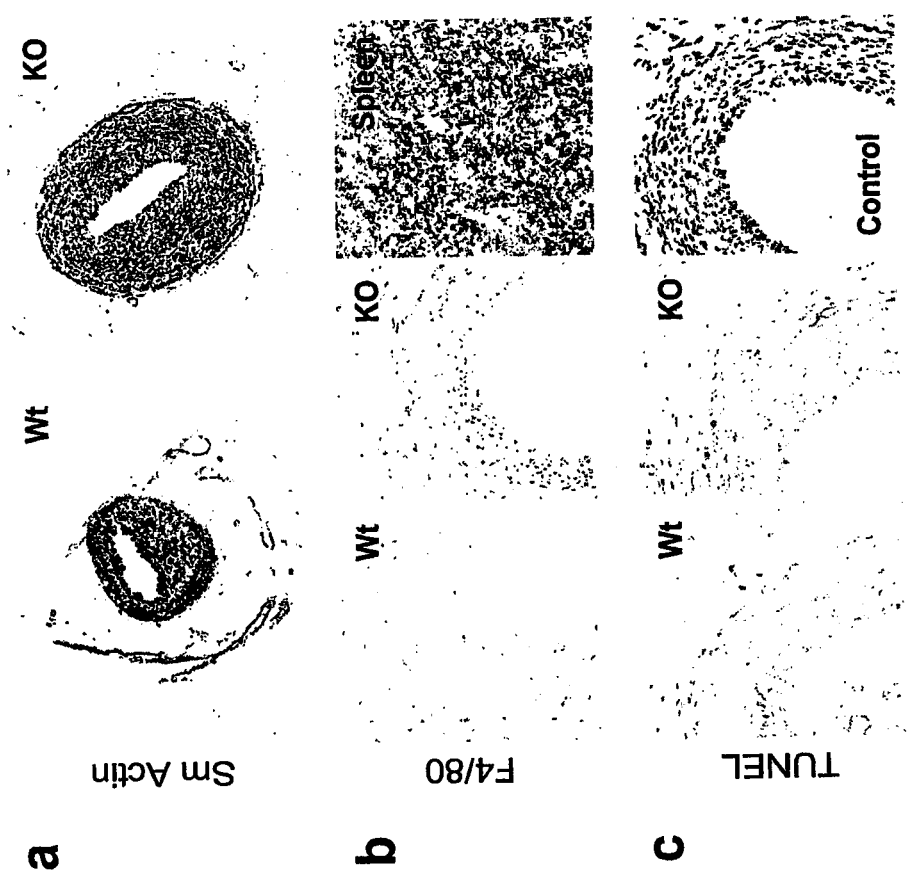

FIG. 11. Immunohistological characterization of neointimal lesions.
a. Wire-injured arteries were stained 5 weeks after the injury with smooth muscle □-actin. Positive staining of the neointimal thickening indicates accumulation of SMC in both wild-type and R-Ras-null lesions. Smooth muscle in the adventitia of small arteries and arterioles is also stained, while adventitial fibroblasts were negative. b. F4/80 staining of the arterial lesions at 3 weeks indicates lack of significant macrophage infiltration in this model. c. TUNEL staining of the lesions at 3 weeks after the injury shows negligible apoptosis of intimal and medial SMC in both wild-type and R-Ras-null lesions. Control, DNase-treated R-Ras-null section as a positive control for TUNEL staining.

Figure 12:
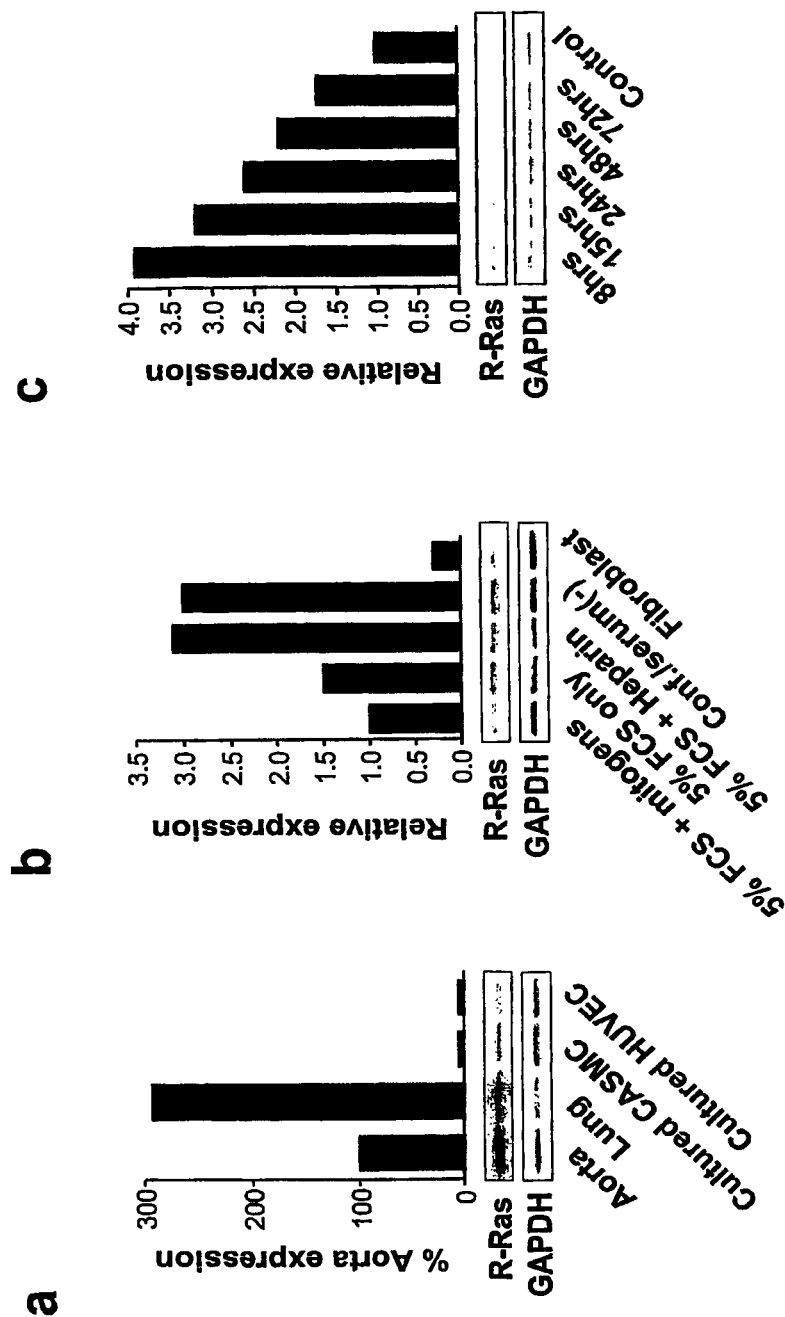

FIG. 12. R-Ras expression is down-regulated significantly in cultured vascular cells.
a. Quiescent vascular cells of aorta (VSMC) and lung (EC) tissues are compared with the proliferating cultured cells for the levels of R-Ras expression. Data is presented as % aorta expression. CASMC, human coronary artery smooth muscle cells. HUVEC, human umbilical cord vein endothelial cells. b. R-Ras expression in CASMC under various culture conditions are presented relative to the level in the proliferating cells in mitogen supplemented media. R-Ras expression increases in differentiation promoting conditions. Conf./serum(-), confluent and serum starved for 5 days. Expression in NIH3T3 fibroblast cells grown in 10% FCS is presented for comparison. c. Up-regulated R-Ras expression in serum-starved CASMC decreases in a time-dependent manner upon mitogen stimulation. Time after the addition of mitogen-supplemented media is indicated. Control, expression level in proliferating cultures.

Figure 13:
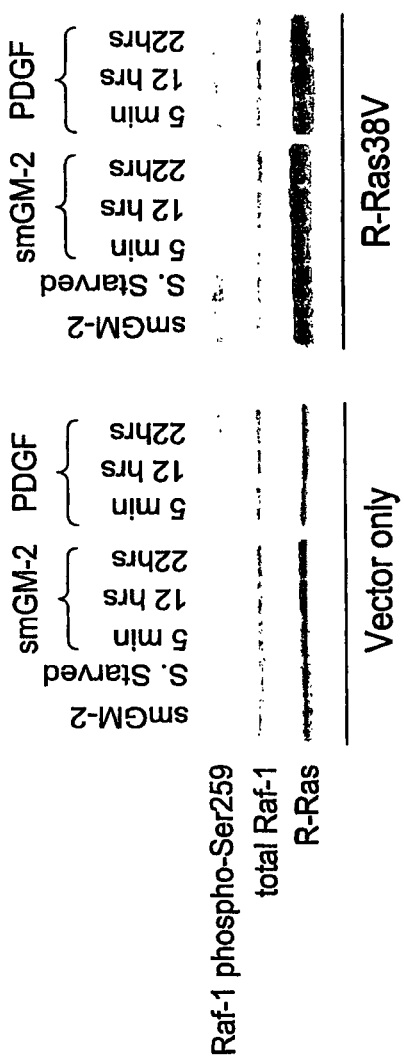

FIG. 13. R-Ras induces Raf-1 phosphorylation in CASMC. Raf-1 phosphorylation at Ser259 was determined in CASMC under different culture conditions. R-Ras increased Raf-1 Ser 259 under all three culture conditions.

FIG. 14. R-Ras wild-type (R-Ras$_{wt}$) sequence and sequences of R-Ras mutants R-Ras 38V and R-Ras 87L.

Figure 15:
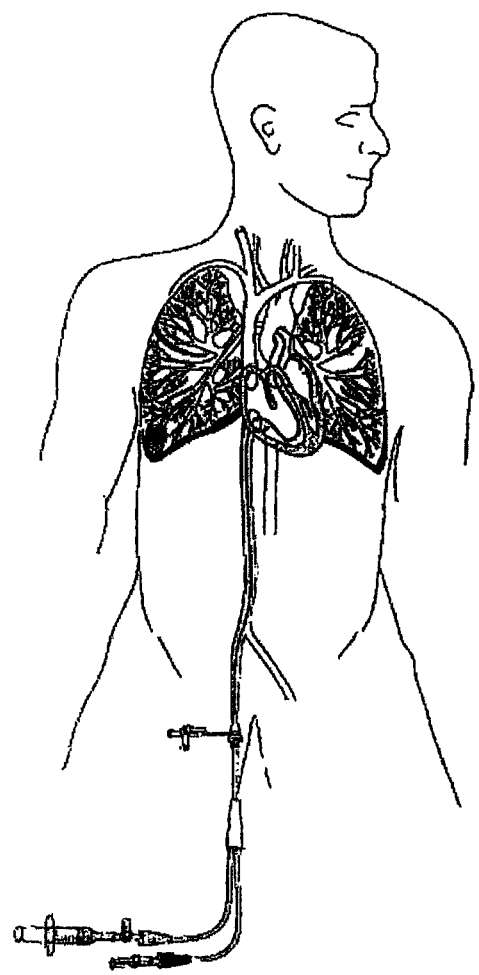

FIG. 15. R-Ras impregnated microparticle catheter directed infusion for lung cancer.

Figure 16:
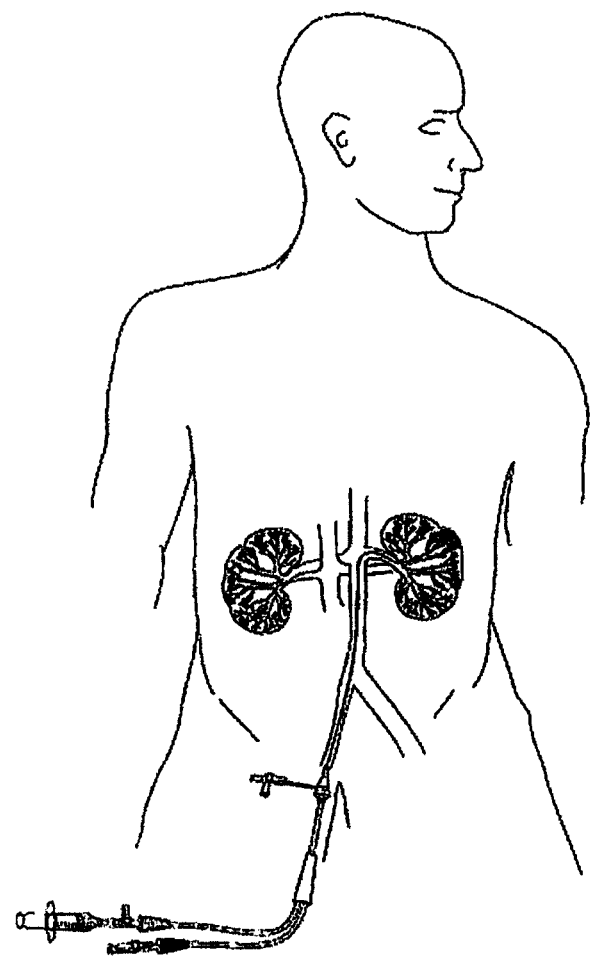

FIG. 16. R-Ras impregnated microparticle catheter directed infusion for kidney cancer.

Figure 17:
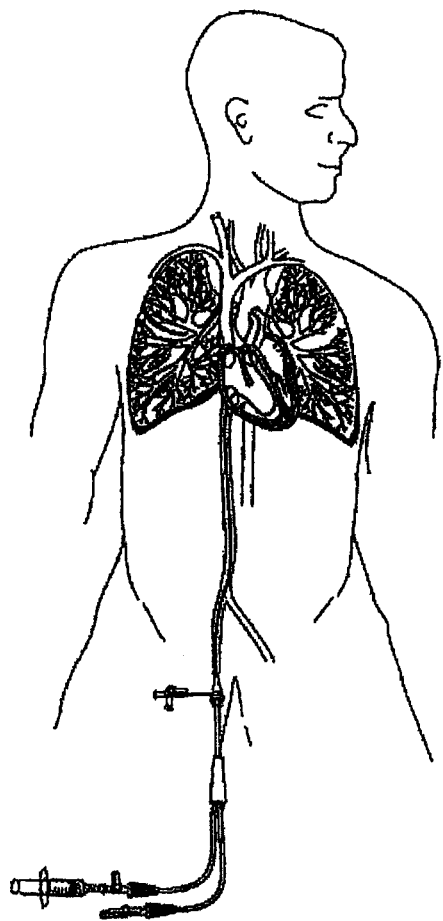

FIG. 17. R-Ras impregnated microparticle catheter directed infusion for pulmonary hypertension.

DETAILED DESCRIPTION OF THE INVENTION

The invention for the first time disclosed a role of R-Ras expression in vascular regulation. In an example of the invention the in vivo function of R-Ras is demonstrated using R-Ras-null mice. Heterozygous intercrosses produced viable offspring with Mendelian distribution of the genotypes. The R-Ras-null mice were fertile and displayed no obvious abnormalities, and their tissues appeared normal upon histological examination. The disruption of R-Ras mRNA and the absence of protein product in null mice were confirmed by RT-PCR, real time RT-PCR, and anti-R-Ras immunoblotting (FIG. 9a-c) as well as by immunohisto-staining assays. The viability of the null mice showed that R-Ras is not essential for mouse embryonic and postnatal development, the existence of alternative pathways apparently compensates the loss of R-Ras. Since there was a lack of any obvious phenotypic abnormalities in the R-Ras null mice, responses to stress were also looked at.

Previously performed mRNA studies indicated that R-Ras is widely expressed throughout various tissues and organs[11]. The invention surprisingly discloses that whereas mRNA of R-Ras is widely present, R-Ras itself has actually a restricted tissue distribution. Antibody staining revealed a restricted tissue distribution for R-Ras, which was primarily confined to smooth muscle in various tissues and organs (FIG. 10a, b). Vascular smooth muscle cells (VSMC) in small arterioles and in major arteries showed intense R-Ras staining, whereas veins were less strongly positive (FIG. 10a, b). R-Ras was distributed along the plasma membrane in the SMC (FIG. 10a, b). Tissues from R-Ras-null mice were negative for R-Ras (FIG. 10c, d). Endothelial cells (EC) of lung capillaries also expressed R-Ras at a high level (FIG. 10e). Lower levels of expression were detected in renal glomeruli (not shown) and the venous endothelium of the spleen (FIG. 10f). All other types of cells, including hepatocytes, neuronal, epithelial, hematopoietic, cardiac muscle, and skeletal muscle were negative or only weakly positive for R-Ras (FIG. 10a, b, f-i). Immunoblotting of tissue extracts with R-Ras-specific antibodies (not shown) gave results consistent with the immunohistology; the highest R-Ras protein content was found in extracts of the aorta, lungs, and intestines. The ubiquitous R-Ras expression detected in previous northern blot and PCR analyses[11] and in our immunoblotting experiments is most likely due to the presence of SMC and EC in every tissue. Potential roles of R-Ras have been examined in vitro in neuronal cells[12] and hematopoietic cells[13]; however, the invention demonstrates that physiological function of this small GTPase would be best characterized in vascular cells, preferably in smooth muscle and endothelial cells.

The invention further determined the developmental pattern of R-Ras expression. All embryonic tissues were negative for R-Ras from E8 (embryonic day 8; the earliest time tested) to E16 (FIG. 11a). The gastrointestinal smooth muscle of E17-18 embryos was the first tissue where R-Ras became detectable (not shown). At birth, the SMC of most organs and tissues expressed low levels of R-Ras, and these levels increased over the first few days (FIG. 11b). R-Ras was also present in neonatal cardiac and skeletal muscle, particularly at myotendinous junctions, whereas adult muscle was negative. R-Ras expression in VSMC and lung capillary ECs was low throughout late embryonic life, with onset of stronger expression at birth. Conversion of developing VSMC into fully differentiated cells is not complete until early in postnatal life[14], and the temporal pattern of R-Ras expression observed in the invention is similar to that of VSMC differentiation markers, such as smooth muscle myosin heavy chain (MHC) and smoothelin[14] (FIG. 11c). These results demonstrate that abundant vascular expression of R-Ras is restricted in the adult to differentiated SMC and to EC of mature vessels. In a preferred embodiment the invention is concerned with R-Ras activity in a postnatal cell.

Figure 1:
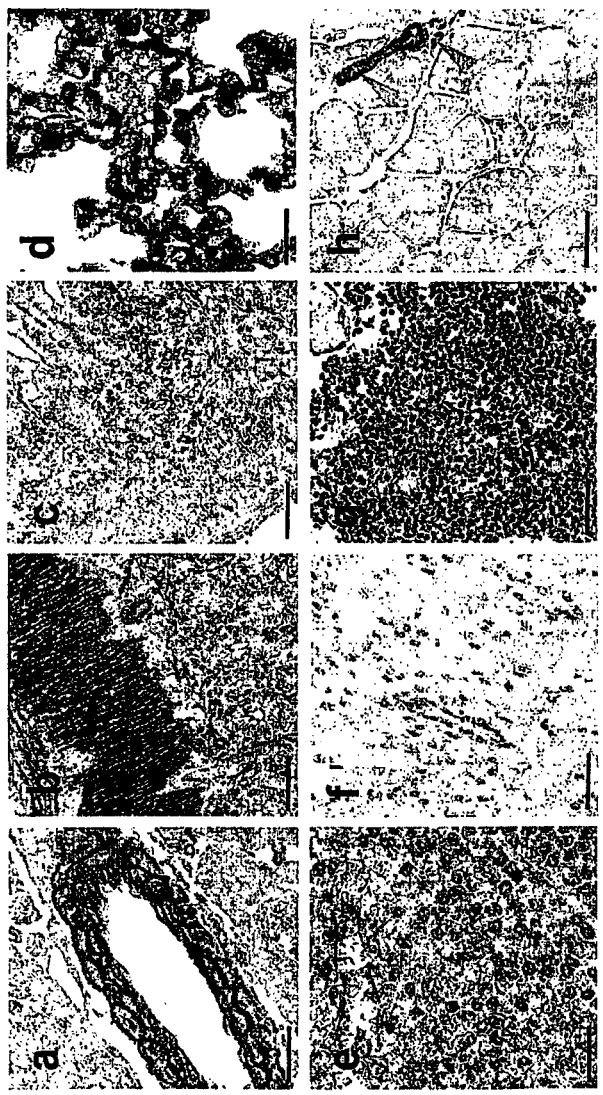
FIG. 1. Immunohistological detection of R-Ras expression in various mouse tissues. Sections of paraffin-embedded mouse tissues were immunostained with rabbit anti-R-Ras polyclonal antibody. Coronary artery and cardiac muscle (a), intestine (b), R-Ras-null intestine (c), lung (d), spleen (e), spinal cord (f), bone marrow (g), and skeletal muscle (h). Scale bar, 20 μm for a, d, e: 50 μm for b, c, and f-h. Arrowheads, arteries; open arrowheads, veins.

The observed spacio-temporal pattern of R-Ras expression demonstrates the regulatory role in the growth and/or homeostasis of the adult vasculature. The model used in the invention to study R-Ras, is commonly used to mimic the restenotic lesions that can develop after angioplasty[15]. Neointimal thickening was found greatly increased in R-Ras-null mice 5 to 6 weeks post injury ($P<1\times10^{-8}$) (FIG. 1a). There was a sustained proliferative response to the arterial injury in the R-Ras-null mice: significant numbers of neointimal cells continued to proliferate in the null mice 3-4 weeks after the injury, whereas in agreement with earlier results[16,17], the proliferation had essentially ceased in the wild-type mice (P<0.02) (FIG. 1b). Notably, R-Ras expression was lost in the wild-type lesions during the hyperplastic phase, and the subsequent mitotic quiescence temporally correlated with resumed R-Ras expression in neointima and media (FIG. 1c). These results support that R-Ras signaling in the regenerating arterial wall negatively regulates smooth muscle hyperplasia. The R-Ras effect on vascular injury was strong relative to other negative regulators of vascular proliferation. In a similar arterial injury model, inactivation of the heme oxygenase-1 gene increased neointimal thickening 2-fold and Brd-U incorporation 6-fold[18]. The corresponding changes in the R-Ras null mice were greater than 3-fold and 10-fold, showing that R-Ras has a profound effect on how vessels respond to injury. Cole et al. recently reported a potential role for R-Ras to enhance inflammatory responses to atherosclerotic and/or restenotic lesions[2]. F4/80 staining of the arterial lesions, however, shows little macrophage association with neointima in both wild-type and R-Ras-null mice (FIG. 12b), demonstrating that the involvement of inflammatory cells in the intimal expansion process is insignificant. Thus, the invention teaches that effects of R-Ras deficiency on inflammatory responses, if any, are overridden by the enhanced neointimal proliferation and VSMC invasion in the R-Ras-deficient lesions.

Figure 2:
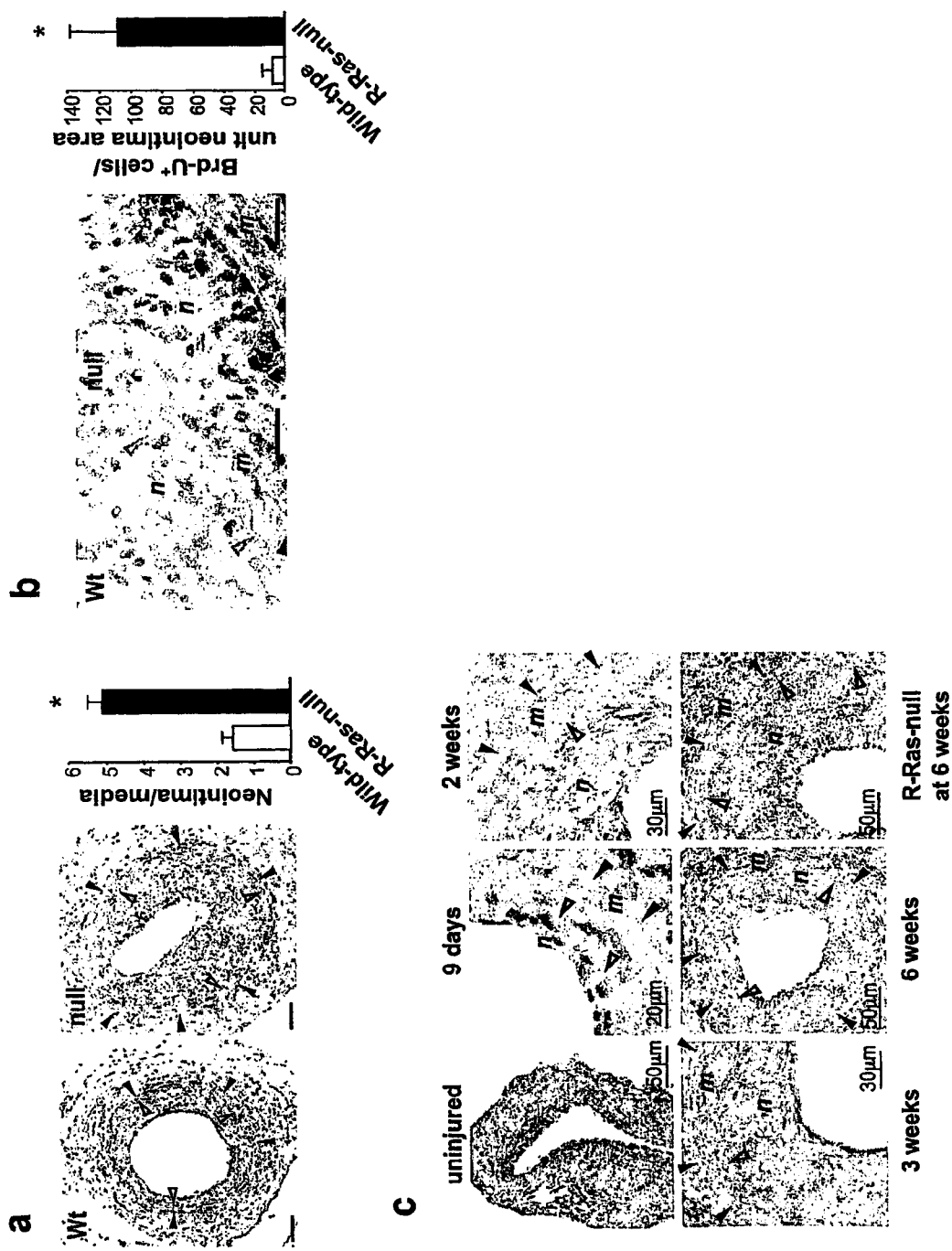
FIG. 2. Enhanced experimental restenosis and sustained neointimal proliferation in R-Ras-null mice. a. Comparison between wild-type (left) and R-Ras-null (center) restenosis at 5 to 6 weeks post injury is presented as neointima:media area ratio (right). $*P<1\times10^{-8}$; n=14 mice per group; scale bar, 50 μm. b. Brd-U staining of 3-week-old lesions and quantification of Brd-U positive cells in neointima. Data is presented as a cumulative result of 3- and 4-week-old lesions. Unit neointima area=0.05 mm$^2$. $*P<0.02$; open arrowheads, internal elastic lamina; scale bar, 20 μm. c. Spatio-temporal pattern of R-Ras expression post arterial injury was determined by immunostaining cross-sections of the injured femoral artery (wild-type) at different time points post injury (9 days to 6 weeks). R-Ras-null lesion provides a control for staining specificity. Open arrowheads, internal elastic lamina; filled arrowheads, external elastic lamina; m, tunica media; n, neointima. Sizes of scale bars are as indicated.

In a non-limiting example of the invention, the effect of absence of R-Ras on angiogenesis was tested. Neovascularization of mouse melanoma B16F10 tumor implants was greatly enhanced in R-Ras-null host mice compared to littermate controls (P=0.001) (FIG. 2a, b). An in vivo matrigel plug angiogenesis assay also revealed higher density of microvessels in the plugs of R-Ras-null mice (P<0.001) (FIG. 2c). Increased endothelial sprouting from ex vivo aortic ring cultures further established the enhanced angiogenic response of the R-Ras-null mice (P<0.02) (FIG. 2d). In wild-type mice, neointimal VSMC and angiogenic EC in tumor vasculature lost their R-Ras expression, as shown for a lung metastasis of mouse mammary tumor in FIG. 2e. Enhanced proliferative EC responses also correlated with the lack of R-Ras expression.

Figure 3:
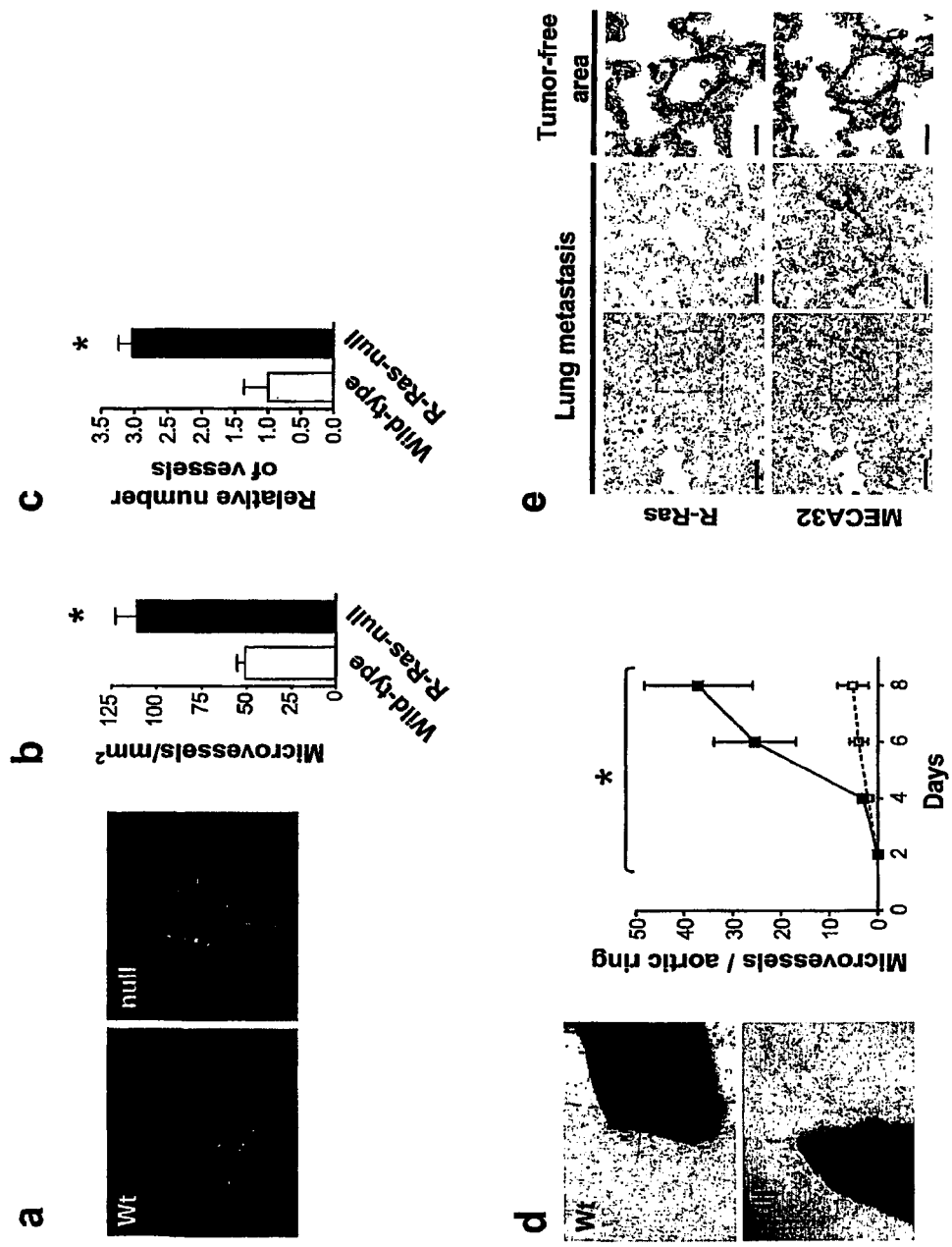
FIG. 3. Angiogenesis is enhanced in R-Ras-null mice. a. Fluorescence microscopy of CD31 (red) and DAPI (blue) staining of B 6F10 mouse melanoma implant at 10 days post implantation. Tumor angiogenesis was significantly enhanced in R-Ras-null mice compared with wild-type host mice. B16F10 mouse melanoma cells ($1\times10^6$) were implanted s.c. into the flank of the mice, and the tumors were excised at 10 days post implantation for analyses. b. Microvessel density in the tumor implant was quantified by counting CD31-positive microvessels. $*p=0.001$. c. Microvessel infiltration into Matrigel plug was enhanced in R-Ras-null mice in response to VEGF. Growth factor reduced Matrigel® containing VEGF and heparin was implanted into the flank of the mice. Seven days later, the Matrigel plugs were harvested and the microvessel infiltration was quantified. $*p<0.001$. d. R-Ras-null EC exhibits the elevated angiogenic response to VEGF in ex vivo aortic ring assays. Representative micrographs of sprouting EC from the wild-type (Wt) aortic ring and R-Ras-null (null) aortic ring at day 6 (left panels). Quantification as number of sprouting microvessels/ring (right). Solid line, R-Ras-null; dashed line, wild-type control. Error bars indicate standard error of mean. $*p<0.02$. e. The expression of R-Ras in angiogenic vessels was determined by immunostaining the 4T1 mouse mammary tumor lung metastases (upper left). An immediately adjacent section (5 μm apart) was stained for the endothelial marker, MECA32, to identify intra-tumor microvessels (lower left). The areas indicated by dashed lines in the left panels are shown at a higher magnification (center). Endothelium of the tumor-free area of the same lung is shown (right). R-Ras expression is not detectable in the tumor neovasculature while it is readily detected in the endothelium of the tumor-free part of the lung. Similar results were obtained from the 4T1 tumor grown in the spleen (not shown). Scale bar, 50 μm for left panels; 20 μm for center and right panels.

The effects of R-Ras expression were further demonstrated in primary cultures of human coronary artery SMC (CASMC). These cells exhibit dedifferentiated features in the presence of growth factor supplements (bFGF, EGF, and IGF), while their growth and migratory behaviors mimic those of VSMC in an atherosclerotic environmente[21]. R-Ras expression in cultured VSMC and human umbilical vein EC (HUVEC) was 2~5% of the levels in intact tissues (FIG. 13a). The expression increased ~3 fold in CASMC when they were cultured in differentiation promoting conditions (FIG. 13b, c). Retrovirus-mediated transduction was used to express activated R-Ras in proliferating CASMC at a level comparable to that in quiescent cells in tissues (FIG. 3a; see Supplementary Methods online). Two forms of activated R-Ras (R-Ras38V and R-Ras 87L) both inhibited cell cycle progression and promoted entry to G0, even in mitogen-rich growth media (FIG. 3b). R-Ras87L was consistently more active in this assay than R-Ras38V, but not in other assays (below). R-Ras also caused increased cell spreading and altered actin organization, both features associated with morphological differentiation of VSMC (FIG. 3c). The effect was similar to but even stronger than that of heparin, a well-known VSMC-differentiating agent[22]. PDGF-induced migration was also substantially inhibited by R-Ras (FIG. 3d). These effects were dependent on R-Ras signaling and not on R-Ras protein expression per se, since no effects were observed when an inactive R-Ras variant (R-Ras43N) was expressed. H-Ras has been shown to enhance the proliferation of VSMC and neointimal thickening[23]. In contrast the invention demonstrates an opposing effect of R-Ras on VSMC.

Figure 4:
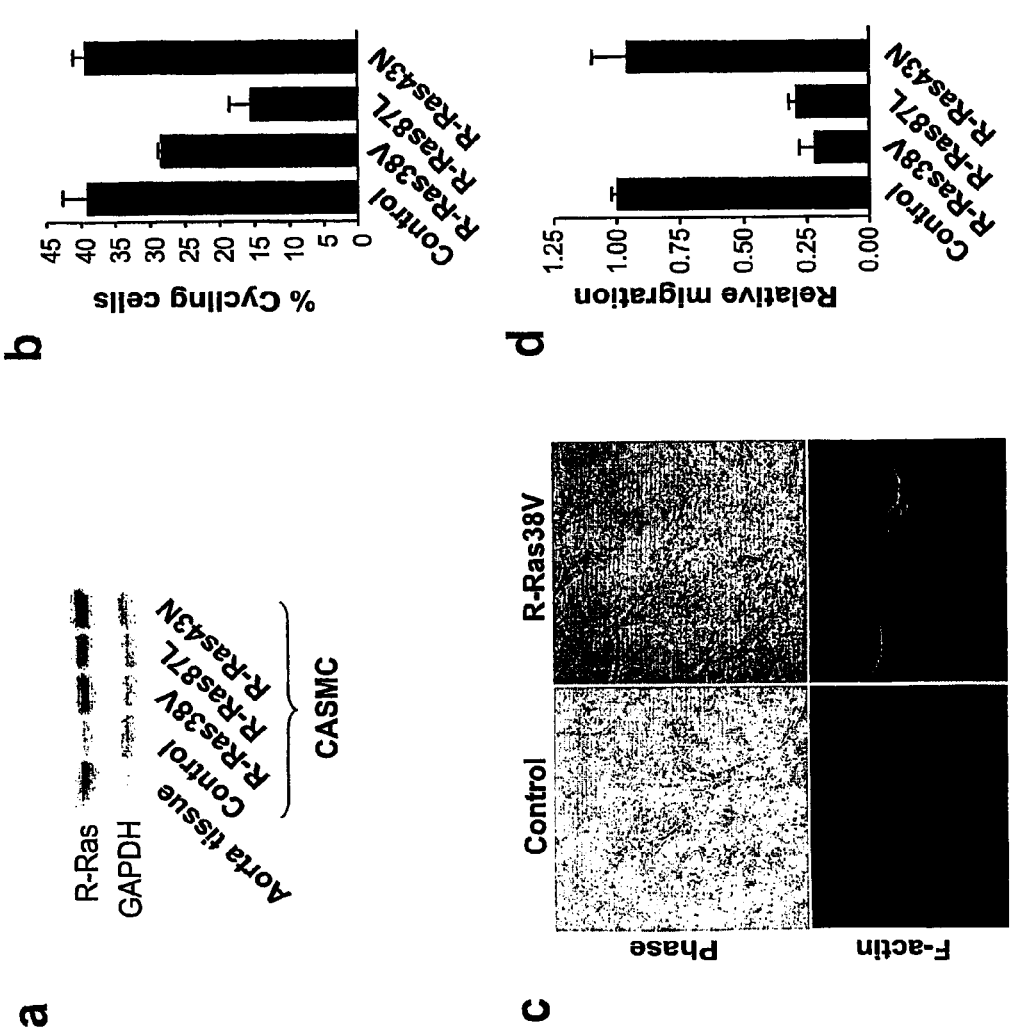
FIG. 4. R-Ras signaling inhibits proliferation and migration and induces extensive morphological differentiation of human coronary artery smooth muscle cells. a, Activated (38V and 87L) and inactive (43N) forms of R-Ras were transduced into cultured CASMC, and the expression levels were compared with endogenous level in aorta tissue and in mock-transduced cells (control). b-d. Activated forms of R-Ras inhibited cell cycle progression (b) and induced morphological differentiation (phase-contrast images and phalloidin staining of filamentous actin) (c) of CASMC cultured in mitogen-rich growth media smGM-2. R-Ras signaling also resulted in the inhibition of cell motility (d). Fraction of cycling cells was determined by Ki-67 staining. PDGF-BB-induced (10 ng/ml) motility was determined using Transwell® culture insert (Costar) coated with 10 μg/ml collagen-I. The data are presented relative to mock transduction control. Error bars indicate standard error of mean.
Figure 5:
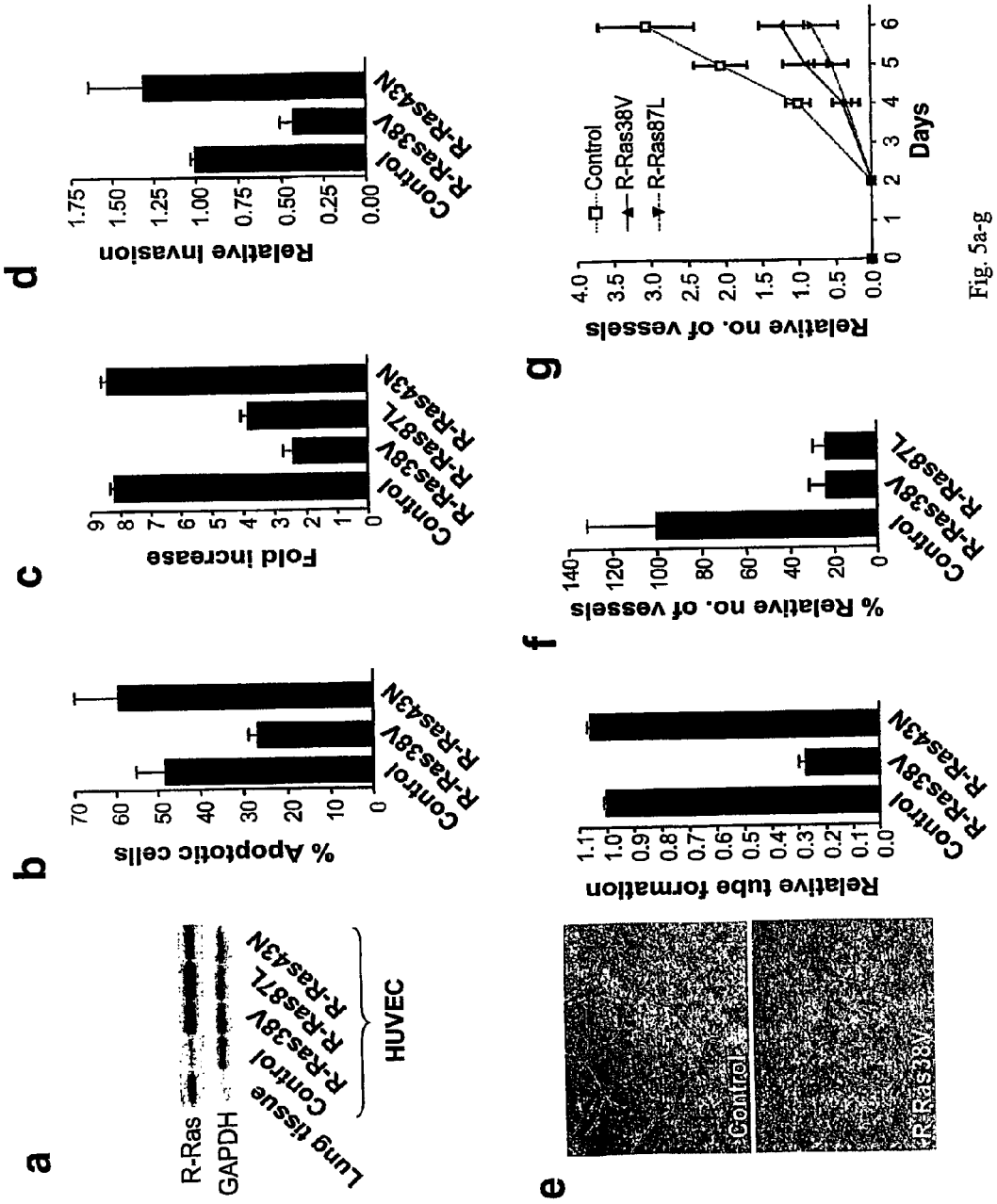
FIG. 5. R-Ras signaling inhibits angiogenic activities, a, Activated and inactive forms of R-Ras were transduced into cultured HUVEC, and the expression levels were compared with endogenous levels in lung tissue and in mock-transduced cells (control). b-d, Activated forms of R-Ras inhibit apoptosis (b) proliferation (c) and invasion (d) of HUVEC. Cells were cultured in low serum (2% horse serum) without mitogen supplementation for 2 days, and percent of apoptotic cells was determined by TUNEL assay. The effect of R-Ras on proliferation was examined in the mitogen-rich endothelial growth media EGM-2. The fold increase during 3-day culture is shown. The invasion assay was performed using Matrigel® invasion chamber with 10 ng/ml bFGF as chemoattractant. e, R-Ras signaling results in the inhibition of tube formation of HUVEC plated on Matrigel®. Left panels, representative micrographs. Right panel, the length of the tubes was measured and expressed relative to mock-transduced control. f. Lentivirus-mediated in vivo delivery of activated R-Ras suppressed VEGF-induced angiogenesis in R-Ras-null mice.

Transduction of activated R-Ras also induced changes in HUVEC (FIG. 4a); the cells spread extensively, becoming extremely flat (not shown) and their survival in low serum cultures was enhanced (FIG. 4b). As with VSMC, R-Ras inhibited the proliferation and invasion of HUVEC (FIG. 4c, d). Furthermore, tube formation (in vitro approximation of angiogenesis) by HUVEC placed on matrigel was greatly diminished by the expression of activated R-Ras (FIG. 4e).

In order to demonstrate that restored R-Ras signaling inhibits angiogenesis, a lentiviral vector was incorporated, carrying an activated R-Ras gene to matrigel plugs. The R-Ras-expressing plugs showed greatly reduced microvessel infiltration (FIG. 4f), showing that exogenous R-Ras can reverse the R-Ras-null vascular phenotype in vivo. Supporting this conclusion further, microvessel outgrowth from the ex vivo culture of R-Ras-null aorta ring was suppressed by the infection with the R-Ras-carrying lentivirus (FIG. 4g).

PI3-kinase-Akt signaling can inhibit Raf activity through phosphorylation of Raf-1 on Ser259 in differentiated myotubes, but not in their myoblast precursors[22]. PI3-kinase is the sole known effector of R-Ras[21]. As R-Ras was in the invention found to be differentially expressed during phenotypic transitions of VSMC and EC, Raf-1 and phosphorylation of its Ser259 residue were found to be central to the R-Ras activities. Transduction of activated R-Ras, but not inactive R-Ras43N or mock transduction, significantly increased Raf-1 Ser259 phosphorylation in both proliferating and quiescent HUVEC and counteracted the transient reduction of Ser259 phosphorylation in mitogen-activated cells (FIG. 6a). Similar changes in Raf-1 phosphorylation were observed in CASMC (FIG. 13). R-Ras signaling did not change the phosphorylation of JNK or Erk1/2 (FIG. 6b). The increase in Raf-1 phosphorylation coincided with R-Ras-dependent Akt activation as indicated by anti-phospho-Akt Ser473 immunoblot (FIG. 6c). R-Ras was a weaker activator of Akt than mitogens or serum, suggesting that R-Ras may activate only a subset of Akt molecules, possibly a subset in focal adhesion complexes, where R-Ras is concentrated[23]. Treatment with Akt inhibitor abolished R-Ras-dependent Raf-1 phosphorylation (FIG. 7).

The functional significance of the R-Ras/Akt-mediated Raf-1 phosphorylation was further studied in the invention, using a serine to alanine substitution at residue 259 (S259A) to prevent inhibitory phosphorylation at this residue[24]. R-Ras effectively inhibited the tube formation of HUVEC expressing wild-type Raf-1, but this effect was significantly reduced in the cells transduced with the S259A Raf-1 mutant (FIG. 8a, b). The S259A mutation of Raf-1 also resulted in significantly reduced R-Ras effect on cell proliferation (FIG. 8c). Akt activation in response to mitogens/serum did not correlate with the enhancement of Raf-1 Ser259 phosphorylation, whereas the Akt activation by R-Ras did. Experiments with an Akt inhibitor also showed that the R-Ras-induced Raf-1 phosphorylation is mediated by Akt. Using the Raf-1 Ser259Ala mutant, it was further demonstrated that the inhibitory effects of R-Ras on EC proliferation and tube formation are indeed, at least in part, mediated through the phosphorylation on Ser259 of Raf-1. In agreement with earlier results showing that R-Ras antagonizes the effects of H-Ras-Raf-1 on integrin activity without affecting Erk MAP-kinase36, it was found that R-Ras inhibition of Raf-1 does not affect Erk MAP-kinase phosphorylation. These results show that R-Ras signaling inhibits Raf-1 regulated events independently of the MEK-Erk pathway. Raf-1 functions independent of MAPkinases have been reported in various biological systems[37].

Taken together, the present invention demonstrates that R-Ras signaling activates a PI3-kinase-Akt pathway that is functionally distinct from the classic growth factor induced PI3-kinase-Akt pathway, and that this signaling pathway produces a unique effect on vascular responses. In addition to the classic pathway, which mediates growth stimulatory signaling, PI3-kinase and Akt can also engage in inhibitory regulation. For instance, PI3-kinase-Akt signaling is essential for skeletal muscle differentiation[38-40], a process that requires cell cycle arrest. In addition, Rommel et al. demonstrated that PI3-kinase-Akt signaling inhibits the H-Ras-Raf pathway, a strong suppressor of myogenic differentiation[11], through Raf-1 Ser259 phosphorylation in differentiated skeletal muscle[22]. R-Ras is known to be abundant in focal adhesions of adherent cells[23], and unlike H- or K-Ras, R-Ras does not migrate out of lipid rafts upon activation[41]. Thus, the functional differences between R-Ras pathway and the classic Ras-PI3-kinase pathway are attributed to the unique subcellular localization of R-Ras, as well as opposing effects of R-Ras and H-Ras on Raf-1.

Example 1

Materials and Methods

Mice. R-Ras-null mice OST24882 were generated by Lexicon Genetics (Woodlands, Tex.) as described before[26]. The inactivation of the R-Ras gene in these mice is caused by an insertion of a gene trap vector VICTR20[26] between exons 4 and 5 of the R-Ras gene on chromosome 7. The insertion disrupted R-Ras gene expression as determined by RT-PCR, real time RT-PCR, and anti-R-Ras immunoblotting of tissue extracts (FIG. 9), as well as immunohistochemistry of tissue sections (FIG. 10). R-Ras mRNA was analyzed by RT-PCR of lung and kidney extracts using a primer set that flanks the knockout vector insertion site between exons 4 and 5 (5'-AGGCAGAGTTTCAATGAGGTGGGCAAGCTC-3', forward (SEQ ID NO:6); 5'-CTCATCGACATTCAGACG-CAGTTG-3', reverse (SEQ ID NO:7)). Real time RT-PCR was done at the Institute's Gene Analysis Facility, using a different primer set, which is specific for exons 3 and 4 (5'-ACAGGCAGAGTTTCAATGAG-3', forward (SEQ ID NO:8); 5'-GTTCTCCAGATCTGCCTTG-3', reverse (SEQ ID NO:9)). Cyclophilin-A mRNA was amplified using specific primers, CACCGTGTTCTTCGACATC (SEQ ID NO:10) and ATTCTGTGAAAGGAGGAACC (SEQ ID NO:11) to normalize real time RT-PCR results, and the relative expression levels of R-Ras mRNA were determined. Heterozygous founder mice with the original mixed genetic background (C57BL6/129Sv) were backcrossed three to five times to C57BL6 (Harlan), and the offspring were intercrossed to produce homozygous and wild-type littermates. All animal experiments were approved by the Institutional Animal Research Committee.

Immunological Detection.

R-Ras expression was determined by standard immunohistochemistry, immunofluorescence, and immunoblotting methods. Rabbit polyclonal antibodies were raised against full-length human R-Ras protein prepared as a GST fusion protein in bacteria[6]. Antibodies were affinity-purified by positive and negative selection on R-Ras and H-Ras affinity columns, respectively. Rabbit antiserum against amino acid 11-31 of mouse R-Ras[27] was a gift from Dr. J. C. Reed of the Burnham Institute for Medical Research. Mouse tissues were fixed with Bouin's solution (Sigma), paraffin embedded, and sectioned for histological analyses. Sections of 8-16 d mouse embryo were obtained from Novagen. Lung metastases were produced by intra-tail vein injection of $1 \times 10^5$ mouse mammary tumor 4T1 cells into the syngeneic (BALB/c) mice. The metastasis-bearing lung was collected 12 d later and fixed in Bouin's solution. Rat monoclonal antibody against pan-endothelial cell antigen, MECA32, (Pharmingen) was used to visualize microvessels in tumor. To examine R-Ras expression in cultured cells, cells were cultured at different conditions, and the expression levels were determined by immunoblot analysis and densitometry. Anti-pan-actin or GAPDH (Chemicon) blot was used to normalize total protein loading. Heparin (Sigma) was used to promote differentiation of VSMC at 200 µg/ml in 5% FCS supplemented media for 3 d. Preparation of histological samples was performed at the Institutional Histological Facility
Experimental Restenosis Model.

Neointimal hyperplasia was produced in mouse femoral artery as described before[17]. After the induction of the vascular injury, the injured vessels were collected at the times indicated. Areas of the media and neointima in the cross-sections of restenotic arteries were calculated by image analysis using Spot System (Universal Imaging Corporation, Downingtown, Pa.). Levels of intimal hyperplasia were presented as neointima:media area ratio. Statistical analysis was performed using Student's t-test (n=14). Proliferation of neointimal cells was assessed by anti-Ki-67 or Brd-U staining after the animals received 1 mg Brd-U/day for two days through i.p. injection prior to collecting the arterial lesion.
Angiogenesis Assays.

Tumor angiogenesis assay, Matrigel plug assay, and ex vivo microvessel outgrowth assay were performed as described elsewhere. Briefly, for subcutaneous tumor implantation, $1 \times 10^6$ B 16F10 mouse melanoma cells were implanted into the flank of the mice, and the tumors were excised at 10 d post implantation for analyses. CD31-positive infiltrating microvessels were counted in five different fields per section from six animals per group. For Matrigel plug assay, growth factor reduced Matrigel® (Becton Dickinson) containing VEGF and heparin was implanted into the flank of the mice. Seven days later, the Matrigel plugs were harvested and the microvessel infiltration was quantified. Assay for endothelial tube formation on Matrigel was carried out using HUVEC as described elsewhere. The efficiency of tube formation was quantified by measuring the total length of the tubes in triplicate wells.
Preparation of Lentivirus for In Vivo Gene Delivery.

The lentiviral vector carrying activated R-Ras (R-Ras38V and R-Ras87L), and the virus with an empty vector (control) were produced according to the manufacturer's manual (Invitrogen). Concentrated virus stocks were prepared by ultracentrifugation of conditioned medium from transfected packaging cells at 50,000×g for 2 h and re-suspending the pellets in PBS using 0.5% of the starting volume. To improve the infection and expression of the transgene, half of the virus stock was incubated with dNTPs for in vitro reverse transcription as described by Naldini et al.[28]. The reverse-transcribed and the original virus stocks were combined and concentrated by a second ultracentrifugation (50,000×g for 90 m). The final pellet was re-suspended in 0.1% of the starting volume of PBS containing 0.5% BSA and 4 g/ml of polybrene, the titer of the virus stock was titrated, and $5 \times 10^6$ TU was used for in vivo experiments.

For the results of example 1 is referred to the detailed description of the invention.

Example 2

This example demonstrates the use of R-Ras as a lung homing vascular anti-proliferative agent for the treatment of patients diagnosed with pulmonary hypertension.

A medicament is formulated by linking R-Ras to Tat (GRKKRRQRRRPPQ (SEQ ID NO:12)), a cell penetrating peptide (ref. 66), and to CGFECVRQCPERC (SEQ ID NO:3), a lung homing peptide (ref. 67). The medicament is administered by injection to patients who meet the criteria for diagnosis of pulmonary hypertension. Such patients show indications of elevated pulmonary artery pressure, a strong indication of blood vessel remodeling due to pulmonary hypertension and its vascular cell proliferative effects.

Example 3

This example demonstrates the use of R-Ras as a vascular anti-proliferative agent in the treatment of patients diagnosed with systemic hypertension and peripheral artery disease secondary to diabetes.

Patients in this example class are in imminent peril of amputation of distal limbs, especially feet and lower legs. On angiographic diagnosis, systemic thickening of arteries appears to be the cause of poor distal circulation. Discrete point blockages which are found in many PVD patients, not just diabetics, are rarely the final cause of diabetic amputation. Discrete point blockages can be successfully removed through a variety of interventional techniques including balloon angioplasty, atherectomy, vein graft bypass, implanted vascular prosthesis, etc. However, these techniques are sometimes contraindicated in severely complicated diabetes patients. A systemically effective medicament is indicated since the distal blockages are smooth, widespread and inoperable. See further ref. 68.

A medicament for the treatment of patients suffering from systemic hypertension and peripheral artery disease secondary to diabetes, said medicament consisting of R-Ras linked to Tat, a cell penetrating peptide. The said medicament is administered at a dose which is effective at reducing vascular cell proliferation of all arteries and restoring natural blood flow.

Alternately, this medicament is used for patients suffering from atherosclerosis and systemic hypertension from unknown causes, or causes other than diabetes Example 4

A method of treating solid organ tumors consisting of controlled release bioabsorbable polymeric microspheres made of poly(lactic-co-glycolic acid) (PLGA) and impregnated with R-Ras linked with F3, an internalizing, tumor-specific homing peptide (KDEPQRRSARLSAKPAPPK-PEPKPKKAPAKK (SEQ ID NO: 13)) (See further refs. 69 and 70). Said microspheres are 10-50 microns in diameter, and are administered by a physician intra-arterially into tumor neovasculature by means of percutaneous catheter based injection (see FIGS. 15 and 16).

Alternately, the bioabsorbable polymeric microspheres are made of polycaprolactone or lactide-co-glycolide polymer impregnated with R-Ras linked with F3.

Example 5

A method of treating pulmonary hypertension consisting of controlled release bioabsorbable polymeric microspheres made of poly(lactic-co-glycolic acid) (PLGA) and impregnated with R-Ras linked with Tat (GRKKRRQRRRPPQ (SEQ ID NO: 12)), a cell penetrating peptide and CGFECVRQCPERC (SEQ ID NO:3), a lung homing peptide. Said microspheres are 10-50 microns in diameter, and are administered by a physician intra-arterially into distal lung vasculature by means of percutaneous catheter based injection (see FIG. 17).

Alternately, the bioabsorbable polymeric microspheres are made of polycaprolactone or lactide-co-glycolide polymer impregnated with R-Ras linked with F3.

Example 6

A chewing gum with composition containing proportions of filler, chewing gum base, emulsifier, gum chicle or SBR synthetic rubber, flavoring, sweetener and the medicament of R-Ras linked with the tumor homing, internalizing peptide F3 to ameliorate medical conditions such as carcinomas of the lips, mouth and tongue due to tobacco use by controlling release of the R-Ras/F3 conjugate during chewing thereof.

Example 7

A topical paste formulated in a hydrophilic petrolatum-based ointment containing R-Ras conjugated to arginine heptamer (RRRRRRRR (SEQ ID NO: 14)), a transporter molecule for the outermost layer of the epidermis, the stratum corneum, for the treatment of spider veins, a disfiguring form of capillaritis. See further reference 71.

The topical paste optionally comprises additional components such as (a) petrolatum or mineral oil, (b) fatty alcohols, (c) fatty ester emollients, (d) silicone oils or fluids, and (e) preservatives. These components must in general be safe for application to the human skin and must be compatible with the other components of the formulation.

Alternately, this topical paste is formulated into a transdermal patch. A transdermal patch is a medicated adhesive patch that is placed on the skin to deliver a time released dose of R-Ras/arginine heptamer conjugate through the skin and into the bloodstream Example 8

This example describes a method of treating restenosis in the coronary arteries after angioplasty or atherectomy procedures with the goal of improving blood flow through the vessels.

This example includes a drug-burdened vascular prosthesis in the tubular form of a stent, coated with bioabsorbable polyglycolic acid which is fused with and contains the following compound: R-Ras linked to Tat, a cell penetrating peptide (see ref. 72), and to a heart homing peptide such as CRPPR (SEQ ID NO:15) (see ref. 73).

Alternately, the stent coatings containing the R-Ras/Tat/CRPPR (SEQ ID NO: 15) conjugate are fused into cellulose, polylactic acid, methacryloyl phosphorylcholine lauryl methacrylate, or a 50/50 mixture of polyethylene vinyl acetate/poly butyl methacrylate.

To deploy the stent, standard angioplasty procedures are used to deliver the stent through the femoral artery or other arterial point of entry. In summary, following identification of the target tissue comprising atheromatous plaque on the wall of the vessel, the stent should be deployed in the area of injury and utilized according to the following steps:

a. the stent-deploying balloon catheter is positioned at the lesion site immediately after the completion of the angioplasty/atherectomy (the protective sheath should be pulled back to expose the drug-laden stent at this point if a sheath was used);

b. the balloon is expanded until the surface of the drug-ladened stent implant fully engages the arterial wall for the full 360.degrees;

d. the balloon is then deflated and all catheters are removed from the body; and e. time released elution of R-Ras/Tat/CRPPR conjugate.

Example 9

In this example, patients with collagen vascular disease are treated in a gene therapy protocol.

Patients suffering from collagen vascular disease experience hyperproliferation of systemic vascular cells causing a variety of debilitating and deadly symptoms. The lack of sufficient R-Ras activity in the vascular cells of the patients is the targeted dysfunction in the gene therapy protocol.

In a first step, an adeno-associated virus, from the parvovirus family, is selected for infection with R-Ras and appropriate enzymes and promoters. Working with a standard protocol for transfection of AAV vectors with desired DNA strands and appropriate joint elements, a gene therapy product is developed.

Patients are provided the gene therapy periodically by percutaneous infusion catheter in a controlled drip application under direct supervision by a physician. As the patient responds to medication, the periods of time between applications lengthen, but do not end.

Alternately, this gene therapy protocol is used for patients suffering from pulmonary hypertension.

Example 10

In this example, R-Ras linked by protein fusion with Tat, an internalizing peptide and a vascular homing peptide are prepared as an aqueous solution for delivering to distal pulmonary capillaries via liposomes for pulmonary dysfunction secondary to Systemic Lupus Erythematosus.

In the example, liposomes are prepared according to standard procedures by dissolving in chloroform the following lipids: 85 mole percent distearyl phosphatidylglycerol (DSPG), mole percent of the disulfide-linked PEG-DSPE conjugate prepared as described in Example 1, 1 mole percent of an affinity moiety-DSPE conjugate, and 4 mole percent cholesterol. The lipids are dried as a thin film by rotation under reduced pressure. The lipid film is hydrated by addition of an aqueous phase to form liposomes which are sized by sonication or by sequential extrusion through Nuclepore polycarbonate membranes with pore sizes of 0.4 .mu.m, 0.2 .mu.m, 0.1 .mu.m and 0.5 .mu.m to obtain liposomes of 100-150 nm in size.

Completed liposomes are introduced into lungs by means of a percutaneous catheter inserted via standard interventional technique to the primary pulmonary artery, where a saline solution containing liposome spheres is released at a controlled rate.

On contacting pulmonary capillary walls, the liposomes dissolve according to a predetermined half-life in normal blood, whereby the local administration of aqueous based drug is absorbed by appropriate hyperproliferated tissues for the relief of SLE related dyspnea and related pulmonary dysfunction.

Example 11

In this example, R-Ras is formulated with the tumor specific, internalizing peptide F3 into nanoparticles for the treatment of solid organ tumors.

Tri-n-octylphosphine oxide-coated ZnS-capped CdSe qdots are synthesized and their surface chemistry modified to render them water soluble. After this, the surface of qdots was coated with mercaptoacetic acid.

R-Ras and F3 (KDEPQRRSARLSAKPAPPKPEPKP-KKAPAKK (SEQ ID NO: 13)) peptide are used to coat the qdots.

The R-Ras and F3 are thiolated by using 3-mercaptopropionimidate hydrochloride (a.k.a. iminothiolane), an imidoester compound containing a sulfhydryl group. R-Ras and F3 are incubated with iminothiolane for 1 h in 10 mM PBS, pH 7.4, at a 1:1 molar ratio. Afterward, mercaptoacetic acid-coated qdots are added to the solution to exchange some of the mercaptoacetic acid groups with the thiolated peptide incubated overnight at room temperature. For co-adsorption of polyethylene glycol (PEG), R-Ras and F3 peptide, amine-terminated PEG (Shearwater Polymers, Huntsville, Ala.) was thiolated with iminothiolane. Thiolated PEG was directly added to a solution of mercaptoacetic acid-coated qdots in 10 mM PBS, pH 7.4, and allowed to incubate overnight at room temperature. PEG helps the qdots maintain solubility in aqueous solvents and minimize nonspecific binding. Afterward, the thiolated peptide are added to the PEG/qdot solution and incubated overnight at room temperature. The coated qdots are purified with Microspin G-50 columns (Amersham Pharmacia) before intravenous injection into the patient.

See further ref. 74.

Example 12

In this example, R-Ras is formulated with the cell penetrating peptide Tat, and lung homing peptide CGFECVRQCPERC (SEQ ID NO:3) into nanoparticles for the treatment of pulmonary hypertension.

Tri-n-octylphosphine oxide-coated ZnS-capped CdSe qdots are synthesized and their surface chemistry modified to render them water soluble. After this, the surface of qdots is coated with mercaptoacetic acid.

R-Ras, cell penetrating peptide Tat, and lung homing peptide CGFECVRQCPERC (SEQ ID NO:3) are used to coat the qdots.

The R-Ras, Tat and CGFECVRQCPERC (SEQ ID NO:3) are thiolated by using 3-mercaptopropionimidate hydrochloride (a.k.a. iminothiolane), an imidoester compound containing a sulfhydryl group. R-Ras, Tat and CGFECVRQCPERC (SEQ ID NO:3) peptides are incubated with iminothiolane for 1 h in 10 mM PBS, pH 7.4, at a 1:1 molar ratio. Afterward, mercaptoacetic acid-coated qdots are added to the solution to exchange some of the mercaptoacetic acid groups with the thiolated peptide incubated overnight at room temperature. For co-adsorption of polyethylene glycol (PEG), R-Ras, Tat and CGFECVRQCPERC (SEQ ID NO:3) peptides, amine-terminated PEG (Shearwater Polymers, Huntsville, Ala.) was thiolated with iminothiolane. Thiolated PEG was directly added to a solution of mercaptoacetic acid-coated qdots in 10 mM PBS, pH 7.4, and allowed to incubate overnight at room temperature. PEG helps the qdots maintain solubility in aqueous solvents and minimize nonspecific binding. Afterward, the thiolated peptide are added to the PEG/qdot solution and incubated overnight at room temperature. The coated qdots are purified with Microspin G-50 columns (Amersham Pharmacia) before intravenous injection into the patient.

Example 13

In this example, R-Ras is formulated with the cell penetrating peptide Tat, and heart homing peptide CRPPR (SEQ ID NO: 15) into nanoparticles for the treatment of coronary artery disease.

Tri-n-octylphosphine oxide-coated ZnS-capped CdSe qdots are synthesized and their surface chemistry modified to render them water soluble. After this, the surface of qdots is coated with mercaptoacetic acid.

R-Ras, cell penetrating peptide Tat, and heart homing peptide CRPPR (SEQ ID NO: 15) are used to coat the qdots.

The R-Ras, Tat and CRPPR (SEQ ID NO: 15) are thiolated by using 3-mercaptopropionimidate hydrochloride (a.k.a. iminothiolane), an imidoester compound containing a sulfhydryl group. R-Ras, Tat and CRPPR (SEQ ID NO: 15) peptides are incubated with iminothiolane for 1 h in 10 mM PBS, pH 7.4, at a 1:1 molar ratio. Afterward, mercaptoacetic acid-coated qdots are added to the solution to exchange some of the mercaptoacetic acid groups with the thiolated peptide incubated overnight at room temperature. For co-adsorption of polyethylene glycol (PEG), R-Ras, Tat and CRPPR (SEQ ID NO: 15) peptides, amine-terminated PEG (Shearwater Polymers, Huntsville, Ala.) was thiolated with iminothiolane. Thiolated PEG was directly added to a solution of mercaptoacetic acid-coated qdots in 10 mM PBS, pH 7.4, and allowed to incubate overnight at room temperature. PEG helps the qdots maintain solubility in aqueous solvents and minimize nonspecific binding. Afterward, the thiolated peptide are added to the PEG/qdot solution and incubated overnight at room temperature. The coated qdots are purified with Microspin G-50 columns (Amersham Pharmacia) before intravenous injection into the patient.

Example 14

This is an example of R-Ras medicaments in an inhaler for the treatment of pulmonary hypertension.

In a solution composition for use in an aerosol inhaler which comprises a R-Ras/Tat/lung homing peptide CGFECVRQCPERC (SEQ ID NO:3) conjugate solution, a propellant such as 1,1,1,2-tetrafluoroethane (HFA 134a), a cosolvent such as alcohol and optionally a low volatility compound the use of a mixture of HFA 134a and HFA 227 allows to modulate the mass median aerodynamic diameter (MMAD) of the aerosol particles on actuation of the inhaler to target specific regions of the respiratory tract. Moreover the fine particle dose (FPD) of the active ingredient in the composition increases by reducing the metering chamber volume. HFAs and in particular 1,1,1,2-tetrafluoroethane (HFA 134a) and 1,1,1,2,3,3,3-heptafluoropropane (HFA 227) have been acknowledged to be the best candidates for non-CFC propellants. Cosolvents which are optionally used in these formulations are for instance alcohols such as ethanol and polyols such as propylene glycol.

For aerosol suspension compositions, a surfactant is often added to improve the physical stability of the suspension. Surfactants also lubricate the valve components in the inhaler device.

The R-Ras conjugate is stored in solution in a pressurized canister. The canister is attached to a plastic, hand-operated pump. When pumped, a certain dose of the R-Ras conjugate is released in aerosol form. The operator puts the release end of the pump into his mouth, and depresses the canister to release the medicine, while simultaneously inhaling deeply. The aerosolized medicine is drawn into the lungs, where it is absorbed into the bronchial alveoli. Peripheral pulmonary deposition of R-Ras conjugates can easily be directly absorbed from the alveoli into the pulmonary circulation.

Alternately, a different approach to aerosol-inhalers is the use of finely divided powdered devices containing standardized amounts (dose) of R-Ras conjugate powder ready for the patient to take.

Example 15

RT-PCR Protocol

Real time PCR methods to determine R-Ras mRNA levels in vascular tissue samples

This example shows a method and features of a clinical laboratory Real Time Polymerase Chain Reaction protocol for the detection and quantification of R-Ras in solid tumor biopsy samples obtained from patients undergoing curative treatment.

R-Ras evaluation can take place in many bodily fluids or tissues; however, in the example endoarterial tissue is selected from either percutaneous or open biopsy.

In an earlier set-up protocol, probe sequences for RNA detection of R-Ras, and common mutations from wild type, are crafted using a reverse DNA transcription.

When biopsy samples arrive at the clinical laboratory, they are prepared for evaluation in AmpliTaq® DNA polymerase (GeneAmp RNA PCR kit, Perkin-Elmer Cetus) according to manufacturer's directions.

As R-Ras levels are detected in patients, reports recommending new treatment decisions are generated for attending physicians that reflect, for example, the need for supplementation of R-Ras in effected tissues, thereby controlling hyperproliferation typical in growing tumors and R-Ras depleted tissues.

See for further details refs. 75 and 76.

Example 16

Production of fusion proteins containing R-Ras in Prokaryotic cells genetically transfected to express R-Ras This example details a method by which R-Ras fusion proteins, with small variations in their structure for various medicinal purposes, are created in quantity using Prokaryotic cells by an inexpensive commercial method.

A fusion protein is a protein created through genetic engineering from two or more proteins/peptides. This is achieved by creating a fusion gene: removing the stop codon from the DNA sequence of the first protein, then appending the DNA sequence of the second protein in frame. That DNA sequence will then be expressed by a cell as a single protein.

After assembling the desired transcript of R-Ras, linkers, homing peptide(s), cell-penetrating peptides, and/or internalizing peptides, the cloned gene is inserted into a pMAL vector down-stream from the malE gene, which encodes maltose-binding protein (MBP). The technique uses the strong Ptac promoter and the translation initiation signals of MBP to express large amounts of the fusion protein. The fusion protein is then purified by one-step affinity purification specific for MBP.

The system uses the pMAL vectors which are designed so that insertion interrupts a lacZα gene allowing a blue-to-white screen for inserts on X-gal (5). The vectors include a sequence coding for the recognition site of a specific protease. This allows the protein of interest to be cleaved from MBP after purification, without adding any vector-derived residues to the protein (6). For this purpose, the polylinker includes a restriction site superimposed on the sequence coding for the site of the specific protease. This is where the gene encoding the fusion protein containing R-Ras is inserted.

Expression from the pMAL vectors yields up to 100 mg fusion protein from a liter of culture. In most cases, the expressed protein is soluble, as fusion to MBP has been proven to enhance the solubility of proteins expressed in *E. coli* (7). In this manner an ideal fusion of R-Ras with both medicinally effective and manufacturable combinations of internalizing peptides and homing peptides can be achieved.

See further references 77-83.

Example 17

In this example, patients presenting unexplained pulmonary hypertension are examined for R-Ras and other protein levels in the smooth muscle cells of their pulmonary arteries.

General diagnosis of suspected pulmonary arterial hypertension is affected by a combination of patient reports of dyspnea, exercise fatigue, and elevated pulmonary artery pressure.

Before directing the patient to an expensive and possibly ineffective regime of pharmacological vasodilatation, anti-proliferatives or surgery, the attending physician in this example orders a histological and molecular diagnosis of the patient's pulmonary arterial wall to assess its health and possible contribution to symptoms.

Using standard cardiovascular intervention technique, tissue is obtained from the patient's arteries using endoarterial biopsy (as described by Rothman A. et al., ref. 84). A portion of the tissue is prepared for histological examination, while another portion is prepared for ELISA testing using a custom pre-fabricated instant ELISA kit, supplied commercially by Bender Medsystems.

In the pre-fabrication of the instant ELISA kit, a panel of proteins with direct or suspected effect on pulmonary hypertension is selected for antibody cloning and testing.

Importantly, one of the proteins in the ELISA kit is R-Ras. A sensitive ELISA test for R-Ras determines its level, not simply its presence.

In the clinical laboratory, prepared samples of a patient's pulmonary artery tissue are tested using the instant ELISA kit, and R-Ras levels for that individual patient's artery wall are determined. Once complete, a report of the test is relayed to the attending physician who determines a treatment regime based on the information. In particular, low or absent R-Ras levels indicate to the physician that R-Ras must be supplemented.

Example 18

Detection of diminished R-Ras activity in pulmonary hypertension by endoarterial biopsy and gene chip microarray.

In this example a pig model of pulmonary hypertension was created via a surgical anastomosis of the left pulmonary artery to the descending aorta (as described by Corno A. et al., ref. 85). After 21 days, endoarterial biopsies were obtained (as described by Rothman A. et al., ref. 86) from the left, hypertensive pulmonary arteries and the right, normotensive pulmonary arteries. RNA was isolated from the endoarterial biopsy samples using an Agilent Total RNA Isolation Micro Kit, and R-Ras gene expression levels in the samples were determined using Affymetrix porcine gene chip microarrays. R-Ras gene expression levels were diminished 58% in the hypertensive endoarterial biopsy samples as compared to the normotensive endoarterial biopsy samples, demonstrating that R-Ras activity is lower in pulmonary hypertensive arteries than in normotensive arteries.

Alternately, this diagnostic technique can be used to detect diminished R-Ras activity in percutaneously obtained atherectomy samples from coronary artery and peripheral artery disease patients.

The diagnostic kit used to perform the endoarterial biopsy described in: "A Kit for Obtaining an Endoarterial Biopsy Sample", WIPO International Publication WO 02/36017, ref. 87; European Patent Application No. 01992532.0, ref. 88; U.S. patent application Ser. No. 10/415,719, ref. 89.

The endoarterial biopsy catheter and endoarterial biopsy method are described in:

U.S. Pat. No. 5,287,857 issued Feb. 22, 1994, Apparatus and Method for Obtaining an Arterial Biopsy, ref. 90; U.S. Pat. No. 5,406,959 issued Apr. 18, 1995, Method and Apparatus for Obtaining an Arterial Biopsy and Diagnosing Diseases of the Vascular System, ref. 91; and European Patent No. 0647121, ref. 92.

Example 19

This example demonstrates the application of R-Ras medicaments to treat or prevent intimal hyperplasia in vascular grafts after surgery (e.g., coronary artery bypass grafts, peripheral artery bypass grafts, organ transplantation, heart valves, etc.).

An isotonic saline solution with a therapeutic dose of R-Ras/Tat conjugate is prepared in advance and made available in the operating theater during transplant operations.

Immediately after blood vessel or organ harvest, or perioperative preparation of tissue-engineered vessels or organs, and prior to surgical implantation, the saline solution is injected into the vessel lumen or lumens so that the inner blood vessel layers are wetted with the solution.

After implantation, the anastomosed vessels are observed according to standard medical practice. If stenosis emerges, several therapeutic options are available to the treating physician.

First is a course of R-Ras pharmacological therapy (see example 2), which is for instance recommended prophylactically prior to observed vessel dysfunction.

Secondly, for example, is atherectomy, followed by an assessment of R-Ras levels in the removed stenotic tissue (see example 15-ELISA), and followed, if appropriate, by additional R-Ras pharmacological therapy.

Thirdly, at post-operative follow-up, diagnosis of the cleared artery by endoarterial biopsy to assess levels of R-Ras in the sampled tissue, and possibly followed up by R-Ras pharmacological therapy.

In every case of pharmacological therapy, if possible, R-Ras is conjugated with the appropriate homing peptides for the dysfunctional vessels.

Example 20

In this example, pulmonary hypertension is treated by ex vivo gene therapy; specifically, dysfunctional pulmonary artery endothelial and smooth muscle cells are modified to produce R-Ras, thereby reducing their dysfunctional hyperplasia, and are then transplanted into original pulmonary arteries.

Endothelial and smooth muscle cells are harvested from a pulmonary hypertension patient by either open or percutaneous biopsy. Harvested cells are modified by adenovirus vector gene therapy protocol to express R-Ras, initially ex vivo.

Once modified, and tested for consistent R-Ras expression, the autologous cells are then reintroduced into the pulmonary arteries by means of percutaneous catheter based injection.

Example 21

This example is a suppository for treatment of anorectal vasculopathies and malignancies. This example demonstrates the embedment of R-Ras linked with Tat, a cell-penetrating peptide, in polycaprolactone (PCL) microspheres for slow-release delivery of R-Ras across mucosal tissues, an application for which the long lasting hydrophobic polymer is particularly suited.

Polycaprolactone (PCL) is a biodegradable, biocompatible and semicrystalline polymer having a very low glass transition temperature. Due to its slow degradation, PCL is ideally suitable for long-term delivery.

Various categories of drugs have been encapsulated in PCL for targeted drug delivery and for controlled drug release. Microspheres of PCL either alone or of PCL copolymers have been prepared to obtain the drug release characteristics.

A solution of R-Ras linked to Tat in ultra-pure water is emulsified with 6% (w/v) solution of PCL (Aldrich) in dichloromethane (UCB, Braine L'Alleud Belgium) using an Ultra turrax model T25 at high speed (8000 rmp) and room temperature. The resulting water-in-oil (w/o) emulsion is then emulsified with 5% (w/v) PVA solution (50 ml) in the same conditions that for the first emulsion to produce a water-in-oil-water (w/o/w) emulsion. The latter is then stirring magnetically at +−800 rpm overnight at room temperature and pressure, to allow the evaporation of the organic solvent and the formation of microparticles. Once their wall was hardened, the microparticles were collected by centrifugation (10 min at 4000×g) washed three times with pure water and freeze-dried. See for example ref. 93.

Microspheres are blended with suppository excipient, poured into plastic molds, and allowed to form. On removal, complete suppositories are wrapped in foil, and made available to treating physicians.

Alternately, these suppositories are used for vaginal and cervical carcinomas.

Example 22

This example shows how to determine the proper dose for a R-Ras medicament:

a. Identify a reasonable starting dose, ideally with specific adjustments (or a firm basis for believing none is needed) for patient size, gender, age, concomitant illness, and concomitant therapy, reflecting an integration of what is known about pharmacokinetic and pharmacodynamic variability.

Depending on circumstances (the disease, the drug's toxicity) the starting dose ranges from a low dose with some useful effect, to a dose that is at or near the full-effect dose.

b. Identify reasonable, response-guided titration steps, and the interval at which they should be taken, again with appropriate adjustments for patient characteristics. These steps would be based either on the shape of the typical individual's dose-effect curves (for both desirable and undesirable effects), if individual dose-response data were available, or if not, on the shape of the population (group)-average dose-response, and the time needed to detect a change in these effects. It should be noted that methodology for finding the population (group)-average dose-response is, at present, better established than is methodology for finding individual dose-response relationships.

c. Identify a dose, or a response (desirable or undesirable), beyond which titration should not ordinarily be attempted because of a lack of further benefit or an unacceptable increase in undesirable effects.

Source and reference: International Conference on Harmonization of Technical Requirements for Registration of Pharmaceuticals for Human Use—10 March 1994

REFERENCES

1. Sethi, T., Ginsberg, M. H., Downward, J. & Hughes, P. E. The small GTP-binding protein R-Ras can influence inte- 1. grin activation by antagonizing a Ras/Raf-initiated integrin suppression pathway. Mol Biol Cell 10, 1799-1809 (1999).
2. Cole, A. L., Subbanagounder, G., Mukhopadhyay, S., Berliner, J. A. & Vora, D. K. Oxidized Phospholipid-Induced Endothelial Cell/Monocyte Interaction Is Mediated by a cAMP-Dependent R-Ras/PI3-Kinase Pathway. Arterioscler Thromb Vase Biol 23, 1384-90 (2003).
3. Lowe, D. G. et al. Structure of the human and murine R-ras genes, novel genes closely related to ras proto-oncogenes. Cell 48, 137-146 (1987).
4. Saez, R., Chan, A. M., Miki, T. & Aaronson, S. A. Oncogenic activation of human R-ras by point mutations analogous to those of prototype H-ras oncogenes. Oncogene 9, 2977-82 (1994).
5. Wang, B., Zou, J. X., Ek-Rylander, B. & Ruoslahti, E. R-Ras contains a proline-rich site that binds to SH3 domains and is required for integrin activation by R-Ras. J Biol Chem 275, 5222-5227 (2000).
6. Zou, J. X. et al. An Eph receptor regulates integrin activity through R-Ras. Proc Natl Acad Sci USA 96, 13813-13818 (1999).
7. Zou, J. X., Liu, Y., Pasquale, E. B. & Ruoslahti, E. Activated SRC oncogene phosphorylates R-ras and suppresses integrin activity. J Biol Chem 277, 1824-7 (2002).
8. Zhang, Z., Vuori, K., Wang, H., Reed, J. C. & Ruoslahti, E. Integrin activation by R-ras. Cell 85, 61-69 (1996).
9. Hughes, P. E. et al. Suppression of integrin activation: a novel function of a Ras/Raf-initiated MAP kinase pathway. Cell 88, 521-530 (1997).
10. Suzuki, J., Kaziro, Y. & Koide, H. Positive regulation of skeletal myogenesis by R-Ras. Oncogene 19, 1138-46 (2000).
11. Ramocki, M. B. et al. Signaling through mitogen-activated protein kinase and Rac/Rho does not duplicate the effects of activated Ras on skeletal myogenesis. Mol Cell Biol 17, 3547-55 (1997).
12. Zambrowicz, B. P. et al. Disruption and sequence identification of 2,000 genes in mouse embryonic stem cells. Nature 392, 608-11 (1998).
13. Pasterkamp, R. J. R-Ras fills another GAP in semaphorin signalling. Trends Cell Biol 15, 61-4 (2005).
14. Ratajska, A., Zarska, M., Quensel, C. & Kramer, J. Differentiation of the smooth muscle cell phenotypes during embryonic development of coronary vessels in the rat. Histochem Cell Biol 116, 79-87 (2001).
15. Carmeliet, P., Moons, L. & Collen, D. Mouse models of angiogenesis, arterial stenosis, atherosclerosis and hemostasis. Cardiovasc Res 39, 8-33 (1998).
16. Clowes, A. W., Reidy, M. A. & Clowes, M. M. Kinetics of cellular proliferation after arterial injury. I. Smooth muscle growth in the absence of endothelium. Lab Invest 49, 327-33 (1983).
17. Sata, M. et al. A mouse model of vascular injury that induces rapid onset of medial cell apoptosis followed by reproducible neointimal hyperplasia. J Mol Cell Cardiol 32, 2097-104 (2000).
18. Moiseeva, E. P. Adhesion receptors of vascular smooth muscle cells and their functions. Cardiovasc Res 52, 372-86 (2001).
19. Weissberg, P. L., Grainger, D. J., Shanahan, C. M. & Metcalfe, J. C. Approaches to the development of selective inhibitors of vascular smooth muscle cell proliferation. Cardiovasc Res 27, 1191-6 (1993).
20. Jin, G. et al. Effects of active and negative mutants of Ras on rat arterial neointima formation. J Surg Res 94, 124-32 (2000).
21. Kinbara, K., Goldfinger, L. E., Hansen, M., Chou, F. L. & Ginsberg, M. H. Ras GTPases: integrins' friends or foes? Nat Rev Mol Cell Biol 4, 767-76 (2003).
22. Rommel, C. et al. Differentiation stage-specific inhibition of the Raf-MEK-ERK pathway by Akt. Science 286, 1738-41 (1999).
23. Furuhjelm, J. & Peranen, J. The C-terminal end of R-Ras contains a focal adhesion targeting signal. J Cell Sci 116, 3729-38 (2003).
24. Zimmermann, S. & Moelling, K. Phosphorylation and regulation of Raf by Akt (protein kinase B). Science 286, 1741-4 (1999).
25. Ehrhardt, A., Ehrhardt, G. R., Guo, X. & Schrader, J. W. Ras and relatives—job sharing and networking keep an old family together. Exp Hematol 30, 1089-106 (2002).
26. Duckers, H. J. et al. Heme oxygenase-1 protects against vascular constriction and proliferation. Nat Med 7, 693-8 (2001).
27. Zhang, Y., Cliff, W. J., Schoefl, G. I. & Higgins, G. Immunohistochemical study of intimal microvessels in coronary atherosclerosis. Am J Pathol 143, 164-72 (1993).
28. Pels, K., Labinaz, M. & O'Brien, E. R. Arterial wall neovascularization—potential role in atherosclerosis and restenosis. Jpn Cire J 61, 893-904 (1997).
29. Hanahan, D. & Folkman, J. Patterns and emerging mechanisms of the angiogenic switch during tumorigenesis. Cell 86, 353-64 (1996).
30. Jain, R. K. Normalization of tumor vasculature: an emerging concept in antiangiogenic therapy. Science 307, 58-62 (2005).
31. Jain, R. K. Molecular regulation of vessel maturation. Nat Med 9, 685-93 (2003).
32. Hood, J. D., Frausto, R., Kiosses, W. B., Schwartz, M. A. & Cheresh, D. A. Differential alphav integrin-mediated Ras-ERK signaling during two pathways of angiogenesis. J Cell Biol 162, 933-43 (2003).
33. Meadows, K. N., Bryant, P. & Pumiglia, K. Vascular endothelial growth factor induction of the angiogenic phenotype requires Ras activation. J Biol Chem 276, 49289-98 (2001).
34. Arbiser, J. L. et al. Oncogenic H-ras stimulates tumor angiogenesis by two distinct pathways. Proc Natl Acad Sci USA 94, 861-6 (1997).
35. Indolfi, C. et al. Inhibition of cellular ras prevents smooth muscle cell proliferation after vascular injury in vivo. Nat Med 1, 541-5 (1995).
36. Hughes, P. E. et al. Suppression of integrin activation by activated Ras or Raf does not correlate with bulk activation of ERK MAP kinase. Mol Biol Cell 13, 2256-65 (2002).
37. Baumann, B. et al. Raf induces NF-kappaB by membrane shuttle kinase MEKK1, a signaling pathway critical for transformation. Proc Natl Acad Sci U S A 97, 4615-20 (2000).
38. Kaliman, P., Vinals, F., Testar, X., Palacin, M. & Zorzano, A. Phosphatidylinositol 3-kinase inhibitors block differentiation of skeletal muscle cells. J Biol Chem 271, 19146-51 (1996).
39. Jiang, B. H., Zheng, J. Z. & Vogt, P. K. An essential role of phosphatidylinositol 3-kinase in myogenic differentiation. Proc Natl Acad Sci USA 95, 14179-83 (1998).
40. Jiang, B. H., Aoki, M., Zheng, J. Z., Li, J. & Vogt, P. K. Myogenic signaling of phosphatidylinositol 3-kinase requires the serine-threonine kinase Akt/protein kinase B. Proc Natl Acad Sci USA 96, 2077-81 (1999).

41. Hansen, M. et al. C-terminal sequences in R-Ras are involved in integrin regulation and in plasma membrane microdomain distribution. Biochem Biophys Res Commun 311, 829-38 (2003).
42. Meadows, K. N., Bryant, P., Vincent, P. A. & Pumiglia, K. M. Activated Ras induces a proangiogenic phenotype in primary endothelial cells. Oncogene 23, 192-200 (2004).
43. Koyama, N. et al. Regulation and function of an activation-dependent epitope of the beta 1 integrins in vascular cells after balloon injury in baboon arteries and in vitro. Am J Pathol 148, 749-61 (1996).
44. Reynolds, L. E. et al. Enhanced pathological angiogenesis in mice lacking beta3 integrin or beta3 and beta5 integrins. Nat Med 8, 27-34 (2002).
45. Cheresh, D. A. & Stupack, D. G. Integrin-mediated death: an explanation of the integrin-knockout phenotype? Nat Med 8, 193-4 (2002).
46. Wang, H. G. et al. R-Ras promotes apoptosis caused by growth factor deprivation via a Bcl-2 suppressible mechanism. J Cell Biol 129, 1103-14 (1995).
47. Christen, T. et al. Cultured porcine coronary artery smooth muscle cells. A new model with advanced differentiation. Circ Res 85, 99-107 (1999).
48. Yi, M., Sakai, T., Fassler, R. & Ruoslahti, E. Antiangiogenic proteins require plasma fibronectin or vitronectin for in vivo activity. Proc Natl Acad Sci USA 100, 11435-8 (2003).
49. Ishida, T. et al. Targeted disruption of endothelial cell-selective adhesion molecule inhibits angiogenic processes in vitro and in vivo. J Biol Chem 278, 34598-604 (2003).
50. Naldini, L., Blomer, U., Gage, F. H., Trono, D. & Verma, I. M. Efficient transfer, integration, and sustained long-term expression of the transgene in adult rat brains injected with a lentiviral vector. Proc Natl Acad Sci USA 93, 11382-8 (1996).
51. Lowe, D. G. Heterologus expression and characterization of the human R-ras gene product. Molecular and cellular biology 8, 2845-2856 (1987).
52. Snyder, E. L., Dowdy, S. F. Cell penetrating peptides in drug delivery. Pharmaceutical Research 3 (2004).
53. Lindgren, M., Hällbrink, M., Prochiantz, A., Langel, U. Cell-penetrating peptides. Elsevier Science Ltd (2000).
54. Temsamani, J., Vidal, P. The use of cell-penetrating peptides for drug delivery. Elsevier Ltd 23 (2004).
55. Hillbrink, M., Florén, A., Elmquist, A., Pooga, M., Bartfai, T., Langel, U. Cargo delivery kinetics of cell-penetrating peptides. Biochimica et Biophysica Acta 1515, 101-109 (2001).
56. Zhang, L., Hoffman, J. A., Ruoslahti, E. Molecular profiling of heart endothelial cells. Circulation 112, 1601-1611 (2005).
57. Rajotte, D., Ruoslahti, E. Membrane dipeptidase is the receptor for a lung-targeting peptide identified by in vivo phage display. J. Biol. Chem. 274, 11593-11598 (1999).
58. Brown, D., Ruoslahti, E. Metadherin, a novel cell-surface protein in breast tumors that mediates lung metastasis. Cancer cell 5, 365-374 (2004).
59. Porkka, K., Laakkonen, P., Hoffman, J. A., Bernasconi, M., and Ruoslahti, E. (2002) Targeting of peptides to the nuclei of tumor cells and tumor endothelial cells in vivo. Proc. Natl. Acad. Sci. USA. 99, 7444-7449.
60. Christian, S., Pilch, J., Porkka, K., Laakkonen, P., and Ruoslahti, E. (2003) Nucleoilin expressed at the cell surface is a marker of endothelial cells in tumor blood vessels. J. Cell Biol. 163, 871-878.
61. Hoffman, J. A., Giraudo E., Singh, M., Inoue, M., Porkka, K., Hanahan D., and Ruoslahti E. (2003) Progressive vascular changes in a transgenic mouse model of squamous cell carcinoma. Cancer Cell 4, 383-391.
62. Joyce, J. A., Laakkonen P., Bemasconi, M., Bergers, G., Ruoslahti, E., and Hanahan, D. (2003) Stage-specific vascular markers revealed by phage display in a mouse model of pancreatic islet tumorigenesis. Cancer Cell 4, 393-403.
63. Laakkonen, P., Porkka, K., Hoffman, J. A., and Ruoslahti, E. (2002) A tumor-homing peptide with a lymphatic vessel-related targeting specificity. Nature Med 8, 743-751.
64. Laakkonen, P., Akerman, M. E., Biliran, H., Yang, M., Ferrer, F., Karpanen, T., Hoffman, R. M., and Ruoslahti, E. (2005) Antitumor activity of a homing peptide that targets tumor lymphatics and tumor cells. Proc. Natl. Acad. Sci. USA. 101, 9381-9386.
65. DeLuca, P. P. Drug delivery system involving interaction between protein or polypeptide and hydrophobic biodegradable polymer. United States patent pub. No. US 2002/0051808.
66. J. Biol. Chem. 1997; 272: 16010-16017.
67. J. Clin. Invest. Volume 102, Number 2, July 1998, 430-437.
68. Clin. Podiatr Med. Surg. 2003 October; 20(4):689-708.
69. Proc. Natl. Acad Sci USA, 2002, May 28; 99 (11):7444-9.
70. J. Cell Biol. 2003 Nov. 24; 163(4):871-8).
71. Nat. Med. 2000 November; 6(11):1253-7.
72. J. Biol. Chem. 1997; 272: 16010-16017.
73. Circulation. 2005; 112:1601-1611.
74. Proc Natl Acad Sci USA. 2002 October 1; 99(20): 12617-21.
75. J. Immunol. Methods. 1997 Dec. 29; 210(2): 195-203.
76. Clinical Chemistry 44: 1161-1169, 1998.
77. Guan, C., Li, P., Riggs, P. D. and Inouye, H. (1987) Vectors that facilitate the expression and purification of foreign peptides in *Escherichia coli* by fusion to maltose-binding protein. Gene, 67, 21-30.
78. Maina, C. V., Riggs, P. D., Grandea, A. G. III, Slatko, B. E., Moran, L. S., Tagliamonte, J. A., McReynolds, L. A. and Guan, C. (1988) Gene, 74, 365-373.
79. Riggs, P. D. (1990) In Expression and Purification of Maltose-Binding Protein Fusions. F. M. Ausebel, R. Brent, R. E. Kingston, D. D. Moore, J. G. Seidman, J. A. Smith and K. Struhl (Eds.), Current Protocols in Molecular Biology, pp. 16.6.1-16.6.10.
80. Kellerman, O. K. and Ferenci, T. (1982) W. A. Wood (Eds.), Methods Enzymol., 90, pp. 459-463. New York: Academic Press.
81. Yanisch-Perron, C., Vieira, J. and Messing J. (1985) Gene, 33, 103-119.
82. LaVallie, E. R. and McCoy, J. M. (1990) F. M. Ausebel, R. Brent, R. E. Kingston, D. D. Moore, J. G. Seidman, J. A. Smith and K. Struhl (Eds.), Current Protocols in Molecular Biology, pp. 16.4.1-16.4.17.
83. Kapust and Waugh (1999) Protein Sci., 8, 1668-1674.
84. Rothman, A. et al. J. Am Coil Cardiol. 1996, 27(1):218-24.
85. Corno, A. et al. Eur J Cardiothorac Surg 2003, 23:513-7.
86. Rohtman, A. et al. J Am Coil Cardiol. 1996, 27(1):218-24.
87. WIPO International Publication WO 02/36017.
88. European Patent Application No. 01992532.0.
89. U.S. patent application Ser. No. 10/415,719.
90. U.S. Pat. No. 5,287,857.
91. U.S. Pat. No. 5,406,959.
92. European Patent No. 0647121.
93. International Journal of Pharmaceutics Volume 278, Issue 1, 18 June 2004, pages 1-23.

94. International Conference on Harmonisation of Technical Requirements for Registration of Pharmaceuticals for Human Use—10 March 1994.
95. U.S. Application No. 2004018605.
96. U.S. Pat. No. 6,835,810.
97. U.S. Pat. No. 6,673,574.
98. U.S. Pat. No. 6,348,185.
99. U.S. Pat. No. 6,759,357.
100. U.S. Pat. No. 6,730,293.
101. U.S. Pat. No. 6,669,951.
102. U.S. Pat. No. 6,593,292.
103. U.S. Pat. No. 6,495,663.
104. U.S. Pat. No. 6,306,993.
105. U.S. Pat. No. 6,933,281.
106. U.S. Pat. No. 6,844,324.
107. U.S. Pat. No. 6,784,153.
108. U.S. Pat. No. 6,610,651.
109. U.S. Pat. No. 6,232,287.
110. U.S. Pat. No. 6,174,687.

The invention claimed is:

1. A method of treating a disease associated with vascular regulation wherein the disease is selected from the group consisting of pulmonary hypertension, systemic hypertension, coronary artery disease, peripheral artery disease secondary to diabetes, solid organ tumors, intimal hyperplasia, ano-rectal vasculopathy, atherosclerosis, postangioplasty restenosis, and capillaritis, comprising:
   1) promoting a quiescent state for a vascular cell, comprising providing said cell with additional R-Ras activity wherein said activity is provided by a R-Ras mutant R-Ras 38V protein; and
   2) administering said R-Ras protein to an individual in need thereof.

2. The method of claim 1, wherein said R-Ras protein is provided with a cell penetrating peptide.

3. The method of claim 1, wherein said R-Ras protein is provided with a homing peptide.

4. The method of claim 1, wherein said R-Ras is used as a medicine.

5. The method of claim 1, wherein said R-Ras protein is coupled with at least one peptide, resulting in a fusion protein.

6. The method of claim 5, wherein the fusion protein comprises said R-Ras protein and a member selected from the group consisting of a Tat-derived protein, a cell penetrating peptide and a homing peptide.

* * * * *

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Synthesized

<400> SEQUENCE: 1

Cys Arg Pro Pro Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Cys Pro Lys Thr Arg Arg Val Pro Cys
1               5

<210> SEQ ID NO 3
<211> LENGTH: 13
<212> TYPE: PRT
<213> ORGANISM: Artificial Sequence
<220> FEATURE:
<223> OTHER INFORMATION: Synthesized

<400> SEQUENCE: 3

Cys Gly Phe Glu Cys Val Arg Gln Cys Pro Glu Arg Cys
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthesized

<400> SEQUENCE: 4

Cys Gly Lys Arg Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Cys Gly Asn Lys Arg Thr Arg Gly Cys
```

-continued

```
<210> SEQ ID NO 6
<211> LENGTH: 30
<212> TYPE: DNA
<213> ORGANISM: Artificial Sequence
<220> FEATURE:
<223> OTHER INFORMATION: Synthesized

<400> SEQUENCE: 6
aggcagagtt tcaatgaggt gggcaagctc                                          30

<210> SEQ ID NO 7
<211> LENGTH: 25
<212> TYPE: DNA
<213> ORGANISM: Artificial Sequence
<220> FEATURE:
<223> OTHER INFORMATION: Synthesized

<400> SEQUENCE: 7
ctcatcgaca ttcagacgca gtttg                                               25

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
acaggcagag tttcaatgag                                                     20

<210> SEQ ID NO 9
<211> LENGTH: 19
<212> TYPE: DNA
<213> ORGANISM: Artificial Sequence
<220> FEATURE:
<223> OTHER INFORMATION: Synthesized

<400> SEQUENCE: 9
gttctccaga tctgccttg                                                      19

<210> SEQ ID NO 10
<211> LENGTH: 19
<212> TYPE: DNA
<213> ORGANISM: Artificial Sequence
<220> FEATURE:
<223> OTHER INFORMATION: Synthesized

<400> SEQUENCE: 10
caccgtgttc ttcgacatc                                                      19

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
attctgtgaa aggaggaacc                                                     20

<210> SEQ ID NO 12
<211> LENGTH: 13
<212> TYPE: PRT
<213> ORGANISM: Artificial Sequence
<220> FEATURE:
```

-continued

<223> OTHER INFORMATION: Synthesized

<400> SEQUENCE: 12

Gly Arg Lys Lys Arg Arg Gln Arg Arg Pro Pro Gln
1               5                   10

<210> SEQ ID NO 13
<211> LENGTH: 31
<212> TYPE: PRT
<213> ORGANISM: Artificial Sequence
<220> FEATURE:
<223> OTHER INFORMATION: Synthesized

<400> SEQUENCE: 13

Lys Asp Glu Pro Gln Arg Arg Ser Ala Arg Leu Ser Ala Lys Pro Ala
1               5                   10                  15
Pro Pro Lys Pro Glu Pro Lys Pro Lys Lys Ala Pro Ala Lys Lys
            20                  25                  30

<210> SEQ ID NO 14
<211> LENGTH: 8
<212> TYPE: PRT
<213> ORGANISM: Artificial Sequence
<220> FEATURE:
<223> OTHER INFORMATION: Synthesized

<400> SEQUENCE: 14

Arg Arg Arg Arg Arg Arg Arg Arg
1               5

<210> SEQ ID NO 15
<211> LENGTH: 5
<212> TYPE: PRT
<213> ORGANISM: Artificial Sequence
<220> FEATURE:
<223> OTHER INFORMATION: Synthesized

<400> SEQUENCE: 15

Cys Arg Pro Pro Arg
1               5

<210> SEQ ID NO 16
<211> LENGTH: 218
<212> TYPE: PRT
<213> ORGANISM: Artificial Sequence
<220> FEATURE:
<223> OTHER INFORMATION: Synthesized

<400> SEQUENCE: 16

Met Ser Ser Gly Ala Ala Ser Gly Thr Gly Arg Gly Arg Pro Arg Gly
1               5                   10                  15
Gly Gly Pro Gly Pro Gly Asp Pro Pro Pro Ser Glu Thr His Lys Leu
            20                  25                  30
Val Val Val Gly Gly Gly Val Gly Lys Ser Ala Leu Thr Ile Gln
        35                  40                  45
Phe Ile Gln Ser Tyr Phe Val Ser Asp Tyr Asp Pro Thr Ile Glu Asp
    50                  55                  60
Ser Tyr Thr Lys Ile Cys Ser Val Asp Gly Ile Pro Ala Arg Leu Asp
65                  70                  75                  80
Ile Leu Asp Thr Ala Gly Gly Glu Glu Phe Gly Ala Met Arg Glu Gln
                85                  90                  95
Tyr Met Arg Ala Gly His Gly Phe Leu Leu Val Phe Ala Ile Asn Asp
                100                 105                 110

-continued

```
Arg Gln Ser Phe Asn Glu Val Gly Lys Leu Phe Thr Gln Ile Leu Arg
        115                 120                 125

Val Lys Asp Arg Asp Asp Phe Pro Val Val Leu Val Gly Asn Lys Ala
    130                 135                 140

Asp Leu Glu Ser Gln Arg Gln Val Pro Arg Ser Glu Ala Ser Ala Phe
145                 150                 155                 160

Gly Ala Ser His His Val Ala Tyr Phe Glu Ala Ser Ala Lys Leu Arg
                165                 170                 175

Leu Asn Val Asp Glu Ala Phe Glu Gln Leu Val Arg Ala Val Arg Lys
            180                 185                 190

Tyr Gln Glu Gln Glu Leu Pro Pro Ser Pro Ser Ala Pro Arg Lys
        195                 200                 205

Lys Gly Gly Gly Cys Pro Cys Val Leu Leu
    210                 215
```

<210> SEQ ID NO 17
<211> LENGTH: 218
<212> TYPE: PRT
<213> ORGANISM: Artificial Sequence
<220> FEATURE:
<223> OTHER INFORMATION: Synthesized

<400> SEQUENCE: 17

```
Met Ser Ser Gly Ala Ala Ser Gly Thr Gly Arg Gly Arg Pro Arg Gly
1               5                   10                  15

Gly Gly Pro Gly Pro Gly Asp Pro Pro Ser Glu Thr His Lys Leu
        20                  25                  30

Val Val Val Gly Gly Val Gly Val Gly Lys Ser Ala Leu Thr Ile Gln
            35                  40                  45

Phe Ile Gln Ser Tyr Phe Val Ser Asp Tyr Asp Pro Thr Ile Glu Asp
    50                  55                  60

Ser Tyr Thr Lys Ile Cys Ser Val Asp Gly Ile Pro Ala Arg Leu Asp
65                  70                  75                  80

Ile Leu Asp Thr Ala Gly Gly Glu Glu Phe Gly Ala Met Arg Glu Gln
                85                  90                  95

Tyr Met Arg Ala Gly His Gly Phe Leu Leu Val Phe Ala Ile Asn Asp
            100                 105                 110

Arg Gln Ser Phe Asn Glu Val Gly Lys Leu Phe Thr Gln Ile Leu Arg
        115                 120                 125

Val Lys Asp Arg Asp Asp Phe Pro Val Val Leu Val Gly Asn Lys Ala
    130                 135                 140

Asp Leu Glu Ser Gln Arg Gln Val Pro Arg Ser Glu Ala Ser Ala Phe
145                 150                 155                 160

Gly Ala Ser His His Val Ala Tyr Phe Glu Ala Ser Ala Lys Leu Arg
                165                 170                 175

Leu Asn Val Asp Glu Ala Phe Glu Gln Leu Val Arg Ala Val Arg Lys
            180                 185                 190

Tyr Gln Glu Gln Glu Leu Pro Pro Ser Pro Ser Ala Pro Arg Lys
        195                 200                 205

Lys Gly Gly Gly Cys Pro Cys Val Leu Leu
    210                 215
```

<210> SEQ ID NO 18
<211> LENGTH: 218
<212> TYPE: PRT
<213> ORGANISM: Artificial Sequence
<220> FEATURE:
<223> OTHER INFORMATION: Synthesized

```
<400> SEQUENCE: 18

Met Ser Ser Gly Ala Ala Ser Gly Thr Gly Arg Gly Arg Pro Arg Gly
1               5                   10                  15

Gly Gly Pro Gly Pro Gly Asp Pro Pro Pro Ser Glu Thr His Lys Leu
            20                  25                  30

Val Val Val Gly Gly Gly Gly Val Gly Lys Ser Ala Leu Thr Ile Gln
            35                  40                  45

Phe Ile Gln Ser Tyr Phe Val Ser Asp Tyr Asp Pro Thr Ile Glu Asp
    50                  55                  60

Ser Tyr Thr Lys Ile Cys Ser Val Asp Gly Ile Pro Ala Arg Leu Asp
65                  70                  75                  80

Ile Leu Asp Thr Ala Gly Leu Glu Glu Phe Gly Ala Met Arg Glu Gln
            85                  90                  95

Tyr Met Arg Ala Gly His Gly Phe Leu Leu Val Phe Ala Ile Asn Asp
            100                 105                 110

Arg Gln Ser Phe Asn Glu Val Gly Lys Leu Phe Thr Gln Ile Leu Arg
            115                 120                 125

Val Lys Asp Arg Asp Asp Phe Pro Val Val Leu Val Gly Asn Lys Ala
    130                 135                 140

Asp Leu Glu Ser Gln Arg Gln Val Pro Arg Ser Glu Ala Ser Ala Phe
145                 150                 155                 160

Gly Ala Ser His His Val Ala Tyr Phe Glu Ala Ser Ala Lys Leu Arg
                165                 170                 175

Leu Asn Val Asp Glu Ala Phe Glu Gln Leu Val Arg Ala Val Arg Lys
            180                 185                 190

Tyr Gln Glu Gln Glu Leu Pro Pro Ser Pro Pro Ser Ala Pro Arg Lys
    195                 200                 205

Lys Gly Gly Gly Cys Pro Cys Val Leu Leu
    210                 215
```